US007922462B2

(12) United States Patent
Preuthun et al.

(10) Patent No.: US 7,922,462 B2
(45) Date of Patent: Apr. 12, 2011

(54) ACTUATOR SYSTEM COMPRISING LEVER MECHANISM

(75) Inventors: Jan Harald Preuthun, Brønshøj (DK); Ole Christian Nielsen, Hillerød (DK); Steffen Hansen, Hillerød (DK); Bjørn Gullak Larsen, Birkerød (DK); Henrik Bengtsson, Taastrup (DK); Leif Johannsen, Odder (DK); Finn Jensen, Hinnerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 71 days.

(21) Appl. No.: 11/541,348

(22) Filed: Sep. 29, 2006

(65) Prior Publication Data
US 2007/0104596 A1 May 10, 2007

Related U.S. Application Data

(63) Continuation of application No. PCT/DK2005/000185, filed on Mar. 18, 2005.

(60) Provisional application No. 60/564,164, filed on Apr. 21, 2004.

(30) Foreign Application Priority Data

Mar. 30, 2004 (DK) ................................ 2004 00507

(51) Int. Cl.
*F04B 17/00* (2006.01)
*A61M 5/142* (2006.01)
(52) U.S. Cl. ..................... 417/413.1; 604/132; 604/152; 604/153
(58) Field of Classification Search .............. 604/132, 604/140, 141, 151, 152, 153; 417/413.1, 417/413.2
See application file for complete search history.

(56) References Cited

U.S. PATENT DOCUMENTS

| 2,605,765 | A | 8/1952 | Kollsman |
| 2,960,097 | A | 1/1957 | Dessau |
| 2,980,032 | A | 2/1959 | Schneider |
| 3,705,601 | A | 12/1972 | Arisland |
| 4,016,879 | A | 4/1977 | Mellor |
| 4,077,405 | A | 3/1978 | Haerten et al. |

(Continued)

FOREIGN PATENT DOCUMENTS

CA 2239457 12/1999

(Continued)

OTHER PUBLICATIONS

Response and Amendment in U.S. Appl. No. 11/540,842, filed Oct. 10, 2008.

(Continued)

*Primary Examiner* — Devon C Kramer
*Assistant Examiner* — Leonard J Weinstein
(74) *Attorney, Agent, or Firm* — Wesley A. Nicolas; Marc A. Began

(57) ABSTRACT

The invention provides a pump assembly comprising an actuator lever, a supporting structure, a pump comprising a pump member moveable by actuation of the actuator lever, and an actuator for moving the actuator lever. A first stationary pivoting joint is formed between the actuator lever and the supporting structure, and a second floating pivoting joint is formed between the actuator lever and the pump member allowing the pump member to float relative to the actuator lever, the floating pivoting point providing a constant-length actuator arm defined between the first pivoting joint and the second pivoting joint.

11 Claims, 18 Drawing Sheets

U.S. PATENT DOCUMENTS

| | | |
|---|---|---|
| 4,137,020 A | 1/1979 | Ito et al. |
| 4,245,634 A | 1/1981 | Albisser et al. |
| 4,262,824 A | 4/1981 | Hrynewycz |
| 4,340,048 A | 7/1982 | Eckenhoff |
| 4,370,305 A | 1/1983 | Affonso |
| 4,378,015 A | 3/1983 | Wardlaw |
| 4,399,824 A | 8/1983 | Davidson |
| 4,402,407 A | 9/1983 | Maly |
| 4,519,792 A | 5/1985 | Dawe |
| 4,529,401 A | 7/1985 | Leslie et al. |
| 4,544,369 A | 10/1985 | Skakoon et al. |
| 4,552,561 A | 11/1985 | Eckenhoff et al. |
| 4,645,491 A | 2/1987 | Evans |
| 4,657,490 A * | 4/1987 | Abbott ............ 417/478 |
| 4,710,170 A | 12/1987 | Haber et al. |
| 4,734,092 A | 3/1988 | Millerd |
| 4,753,651 A | 6/1988 | Eckenhoff |
| 4,755,173 A | 7/1988 | Konopka et al. |
| 4,788,556 A | 11/1988 | Hoisington et al. |
| 4,871,351 A | 10/1989 | Feingold |
| 4,877,034 A | 10/1989 | Atkins et al. |
| 4,886,499 A | 12/1989 | Cirelli et al. |
| 4,894,054 A | 1/1990 | Miskinyar |
| 4,928,528 A | 5/1990 | Marques |
| 4,994,078 A | 2/1991 | Jarvik |
| 5,008,110 A | 4/1991 | Benecke et al. |
| 5,049,146 A | 9/1991 | Bringham et al. |
| 5,076,890 A | 12/1991 | Balembois |
| 5,122,116 A | 6/1992 | Kriesel et al. |
| 5,122,201 A | 6/1992 | Frazier et al. |
| 5,149,340 A | 9/1992 | Waycuilis |
| 5,169,390 A | 12/1992 | Athayde et al. |
| 5,211,201 A | 5/1993 | Kamen et al. |
| 5,224,843 A | 7/1993 | van Lintel |
| 5,256,157 A | 10/1993 | Samiotes et al. |
| 5,336,052 A | 8/1994 | Zollner et al. |
| 5,390,671 A | 2/1995 | Lord et al. |
| 5,391,950 A | 2/1995 | Krawczak |
| 5,482,473 A | 1/1996 | Lord et al. |
| 5,485,917 A | 1/1996 | Early |
| 5,494,415 A | 2/1996 | Morita |
| 5,514,095 A | 5/1996 | Brightbill et al. |
| 5,527,287 A | 6/1996 | Miskinyar |
| 5,527,288 A | 6/1996 | Gross et al. |
| 5,568,806 A | 10/1996 | Cheney, II et al. |
| 5,584,808 A | 12/1996 | Healy |
| 5,584,813 A | 12/1996 | Livingston et al. |
| 5,586,085 A | 12/1996 | Lichte |
| 5,609,572 A | 3/1997 | Lang |
| 5,647,853 A | 7/1997 | Feldmann et al. |
| 5,720,391 A | 2/1998 | Dohm et al. |
| 5,776,109 A | 7/1998 | Urrutia |
| 5,814,020 A | 9/1998 | Gross |
| 5,851,197 A | 12/1998 | Marano et al. |
| 5,858,001 A | 1/1999 | Tsals et al. |
| 5,860,952 A | 1/1999 | Quinn |
| 5,913,856 A | 6/1999 | Chia et al. |
| 5,925,017 A | 7/1999 | Kriesel et al. |
| 5,928,194 A | 7/1999 | Maget |
| 5,931,814 A | 8/1999 | Alex et al. |
| 5,941,611 A * | 8/1999 | Trzmiel et al. ............ 303/115.2 |
| 5,954,643 A | 9/1999 | VanAntwerp et al. |
| 5,957,895 A | 9/1999 | Sage et al. |
| 5,968,011 A | 10/1999 | Larsen et al. |
| 5,997,501 A | 12/1999 | Gross et al. |
| 6,045,534 A | 4/2000 | Jacobsen et al. |
| 6,060,319 A | 5/2000 | Deetz et al. |
| 6,074,369 A | 6/2000 | Sage et al. |
| 6,083,196 A | 7/2000 | Trautman et al. |
| 6,088,619 A | 7/2000 | Hein et al. |
| 6,099,512 A | 8/2000 | Urrutia |
| 6,120,492 A | 9/2000 | Finch et al. |
| 6,123,519 A | 9/2000 | Kato et al. |
| 6,126,637 A | 10/2000 | Kriesel et al. |
| 6,132,755 A | 10/2000 | Eicher et al. |
| 6,165,155 A | 12/2000 | Jacobsen et al. |
| 6,241,704 B1 | 6/2001 | Peterson et al. |
| 6,270,478 B1 | 8/2001 | Mernøe |
| 6,280,148 B1 | 8/2001 | Zengerle et al. |
| 6,293,925 B1 | 9/2001 | Safabash et al. |
| 6,302,866 B1 | 10/2001 | Marggi |
| 6,302,869 B1 | 10/2001 | Klitgaard |
| 6,358,731 B1 | 3/2002 | Hsu |
| 6,364,865 B1 | 4/2002 | Lavi et al. |
| 6,485,461 B1 | 11/2002 | Mason et al. |
| 6,500,150 B1 | 12/2002 | Gross et al. |
| 6,551,276 B1 | 4/2003 | Mann et al. |
| 6,554,791 B1 | 4/2003 | Cartledge et al. |
| 6,555,986 B2 | 4/2003 | Moberg |
| 6,558,351 B1 | 5/2003 | Steil et al. |
| 6,589,229 B1 | 7/2003 | Connelly et al. |
| 6,613,015 B2 | 9/2003 | Sandstrom et al. |
| 6,622,037 B2 | 9/2003 | Kasano |
| 6,656,159 B2 | 12/2003 | Flaherty |
| 6,716,192 B1 | 4/2004 | Orosz |
| 6,740,059 B2 | 5/2004 | Flaherty |
| 6,749,587 B2 | 6/2004 | Flaherty |
| 6,808,691 B1 | 10/2004 | Herve et al. |
| 6,818,178 B2 | 11/2004 | Kohl et al. |
| 6,878,136 B2 | 4/2005 | Fleury et al. |
| 6,949,084 B2 | 9/2005 | Marggi et al. |
| 6,960,192 B1 | 11/2005 | Flaherty et al. |
| 7,052,483 B2 | 5/2006 | Wojcik |
| 7,070,580 B2 | 7/2006 | Nielsen |
| 7,097,631 B2 | 8/2006 | Trautman et al. |
| 7,097,690 B2 | 8/2006 | Usher et al. |
| 7,141,023 B2 | 11/2006 | Diermann et al. |
| 7,144,384 B2 | 12/2006 | Gorman et al. |
| 7,303,073 B2 | 12/2007 | Raynal-Olive et al. |
| 7,744,570 B2 | 6/2010 | Fangrow |
| 2001/0025168 A1 | 9/2001 | Gross et al. |
| 2002/0040083 A1 | 4/2002 | Kuwaki et al. |
| 2002/0040208 A1 | 4/2002 | Flaherty et al. |
| 2002/0055711 A1 | 5/2002 | Lavi et al. |
| 2002/0064468 A1* | 5/2002 | Wade ............ 417/233 |
| 2002/0123740 A1 | 9/2002 | Flaherty et al. |
| 2002/0161332 A1 | 10/2002 | Ramey |
| 2002/0169416 A1 | 11/2002 | Gonnelli et al. |
| 2003/0009131 A1 | 1/2003 | Van Antwerp et al. |
| 2003/0009133 A1 | 1/2003 | Ramey |
| 2003/0029501 A1 | 2/2003 | Williamson et al. |
| 2003/0060781 A1 | 3/2003 | Mogensen et al. |
| 2003/0065308 A1 | 4/2003 | Lebel et al. |
| 2003/0069546 A1 | 4/2003 | Sandstrom et al. |
| 2003/0073952 A1 | 4/2003 | Flaherty et al. |
| 2003/0088238 A1 | 5/2003 | Poulsen et al. |
| 2003/0114797 A1 | 6/2003 | Vaillancourt et al. |
| 2003/0135159 A1 | 7/2003 | Daily et al. |
| 2003/0167035 A1* | 9/2003 | Flaherty et al. ............ 604/67 |
| 2003/0187395 A1 | 10/2003 | Gabel et al. |
| 2003/0194328 A1 | 10/2003 | Bryant et al. |
| 2003/0199823 A1 | 10/2003 | Bobroff et al. |
| 2003/0216686 A1 | 11/2003 | Lynch et al. |
| 2003/0236498 A1* | 12/2003 | Gross et al. ............ 604/141 |
| 2004/0051674 A1 | 3/2004 | Mahringer |
| 2004/0087240 A1 | 5/2004 | Chen et al. |
| 2004/0098068 A1 | 5/2004 | Carbunaru et al. |
| 2004/0115068 A1 | 6/2004 | Hansen et al. |
| 2004/0116905 A1 | 6/2004 | Pedersen et al. |
| 2004/0127844 A1 | 7/2004 | Flaherty |
| 2004/0158207 A1 | 8/2004 | Hunn et al. |
| 2004/0162521 A1 | 8/2004 | Bengtsson |
| 2004/0171403 A1 | 9/2004 | Mikkola |
| 2004/0199123 A1 | 10/2004 | Nielsen |
| 2004/0204673 A1 | 10/2004 | Flaherty et al. |
| 2004/0220497 A1 | 11/2004 | Findlay et al. |
| 2004/0220536 A1 | 11/2004 | VanTassel et al. |
| 2004/0260233 A1 | 12/2004 | Garibotto et al. |
| 2005/0006309 A1 | 1/2005 | Effenhauser et al. |
| 2005/0022274 A1 | 1/2005 | Campbell et al. |
| 2005/0077225 A1 | 4/2005 | Usher et al. |
| 2005/0101933 A1 | 5/2005 | Marrs et al. |
| 2005/0171513 A1 | 8/2005 | Mann et al. |
| 2005/0203461 A1* | 9/2005 | Flaherty et al. ............ 604/131 |
| 2005/0240154 A1 | 10/2005 | Mogensen et al. |
| 2006/0015063 A1 | 1/2006 | Butikofer et al. |
| 2006/0017576 A1 | 1/2006 | Gordon et al. |

| | | | |
|---|---|---|---|
| 2006/0020300 | A1 | 1/2006 | Nghiem et al. |
| 2006/0142698 | A1 | 6/2006 | Ethelfeld |
| 2006/0200073 | A1 | 9/2006 | Radmer et al. |
| 2006/0264835 | A1 | 11/2006 | Nielsen et al. |
| 2007/0021733 | A1 | 1/2007 | Hansen et al. |
| 2007/0073228 | A1 | 3/2007 | Mernoe et al. |
| 2007/0104596 | A1 | 5/2007 | Preuthun et al. |
| 2007/0112301 | A1 | 5/2007 | Preuthun et al. |
| 2008/0009805 | A1 | 1/2008 | Ethelfeld |
| 2009/0163874 | A1 | 6/2009 | Krag et al. |

FOREIGN PATENT DOCUMENTS

| | | |
|---|---|---|
| CN | 1612758 | 5/2005 |
| DE | 2552446 | 5/1977 |
| DE | 10255817 | 6/2004 |
| DK | PA 2003 00696 | 5/2003 |
| DK | PA 2003 00697 | 5/2003 |
| EP | 568176 A1 | 11/1993 |
| EP | 398583 B1 | 4/1994 |
| EP | 937475 | 8/1999 |
| EP | 1177802 | 7/2000 |
| EP | 1256356 | 11/2002 |
| EP | 1329233 | 7/2003 |
| EP | 1475113 | 11/2004 |
| EP | 1527792 | 5/2005 |
| GB | 2020735 | 5/1978 |
| GB | 2212387 | 7/1989 |
| JP | 2000-104659 | 4/2000 |
| JP | 2000-513259 | 10/2000 |
| JP | 2000-515394 | 11/2000 |
| JP | 2002-505601 | 2/2002 |
| WO | WO 90/07942 | 7/1990 |
| WO | WO 96/07397 | 3/1996 |
| WO | WO 96/30679 | 10/1996 |
| WO | WO 97/21457 | 6/1997 |
| WO | WO 98/57683 | 12/1998 |
| WO | WO 99/62576 | 12/1999 |
| WO | WO 02/02165 | 1/2002 |
| WO | WO 02/04048 A3 | 1/2002 |
| WO | WO 02/05889 | 1/2002 |
| WO | WO 02/15889 | 2/2002 |
| WO | WO 02/15965 | 2/2002 |
| WO | WO 02/40083 | 5/2002 |
| WO | WO 02/45574 | 6/2002 |
| WO | WO 02/47746 | 6/2002 |
| WO | WO 02/055132 | 7/2002 |
| WO | WO 02/070024 | 9/2002 |
| WO | WO 02/081012 | 10/2002 |
| WO | WO 02/100457 | 12/2002 |
| WO | WO 03/026726 | 4/2003 |
| WO | WO 03/026728 | 4/2003 |
| WO | WO 03/080169 | 10/2003 |
| WO | WO 03/089028 | 10/2003 |
| WO | WO 03/090509 | 11/2003 |
| WO | WO 03/099358 | 12/2003 |
| WO | WO 2004/009160 | 1/2004 |
| WO | WO 2004009160 A1 * | 1/2004 |
| WO | 2004/029457 | 4/2004 |
| WO | WO 2004/030728 | 4/2004 |
| WO | WO 2004/098682 | 11/2004 |
| WO | WO 2004/098683 | 11/2004 |
| WO | WO 2004/098684 | 11/2004 |
| WO | WO 2004/101071 | 11/2004 |
| WO | WO 2005/002649 | 1/2005 |
| WO | WO 2005/011779 | 2/2005 |
| WO | WO 2005/025652 | 3/2005 |
| WO | WO 2005/037185 | 4/2005 |
| WO | WO 2005/037350 | 4/2005 |
| WO | WO 2005/039673 | 5/2005 |
| WO | WO 2005/094919 | 10/2005 |
| WO | WO 2005/123186 | 12/2005 |
| WO | WO 2005/123189 | 12/2005 |
| WO | WO 2006/060277 | 6/2006 |
| WO | WO 2006/067217 | 6/2006 |
| WO | WO 2006/077263 | 7/2006 |
| WO | WO 2006/089958 | 8/2006 |
| WO | WO 2006/120253 | 11/2006 |
| WO | WO 2006/123329 | 11/2006 |
| WO | WO 2007/122207 | 11/2007 |
| WO | WO 2009/021950 | 2/2009 |

OTHER PUBLICATIONS

Office Action in U.S. Appl. No. 11/540,842, send from the USPTO on Dec. 12, 2008.
Response and Amendment in U.S. Appl. No. 11/540,842, filed Mar. 11, 2009.
Final Office Action in U.S. Appl. No. 11/540,842, send from the USPTO on May 13, 2009.
Response and Amendment in U.S. Appl. No. 11/540,842, filed Aug. 7, 2009.
Non-Final Office Action mailed Sep. 28, 2009 in U.S. Appl. No. 11/540,842, filed Sep. 29, 2006 by Preuthun et al.
Office Action in U.S. Appl. No. 11/540,842, sent from the USPTO on Feb. 25, 2008.
Response and Amendment in U.S. Appl. No. 11/540,842, filed May 20, 2008.
Office Action in U.S. Appl. No. 11/540,842, send from the USPTO on Jul. 11, 2008.
International Search Report mailed Jul. 5, 2007 in international application No. PCT/EP2007/053923.
International Preliminary Examination Report issued in connection with counterpart PCT Application No. PCT/EP2006/062301, mailed Nov. 22, 2007.
International Search Report and Written Opinion issued in connection with counterpart international application No. PCT/EP2006/062301, mailed Nov. 2, 2006.
International Search Report mailed May 24, 2006 in international application No. PCT/EP2006/050410.
Office Action Issued in Connection With Counterpart Danish Application No. PA 2005 00703, Mailed Mar. 3, 2006.
CN 1612758 English Abstract, published Feb. 6, 2008.
DE 10255817 English Abstract, published Jun. 17, 2004.
DE 2552446 English Abstract, published May 26, 1977.
JP 2002-505601 Machine Translation, published Feb. 19, 2002.
JP 2000-515394 Machine Translation, published Nov. 21, 2000.
JP 2000-513259 Machine Translation, published Oct. 10, 2000.
JP 2000-104659 Machine Translation, published Apr. 11, 2000.
Final Office Action mailed May 5, 2010 in U.S. Appl. No. 11/540,842, filed Sep. 29, 2006 by Preuthun et al.
US 6,197,009, 03/2001, Steg (withdrawn)

* cited by examiner

ACTUATOR SYSTEM COMPRISING LEVER MECHANISM

CROSS REFERENCE TO RELATED APPLICATIONS

This application is a continuation of international application no. PCT/DK2005/000185 filed Mar. 18, 2005 and claims priority of Danish application no. PA 2004 00507 filed Mar. 30, 2004 and U.S. provisional application Ser. No. 60/564,164 filed Apr. 21, 2004 all of which are hereby incorporated by reference.

FIELD OF THE INVENTION

The present invention relates to actuators suitable for actuation of pumps for the delivery of fluids. In a specific aspect, the invention relates to an actuator system suitable for actuating a membrane pump arranged in a drug delivery device adapted to be carried by a person. However, the present invention may find broad application in any field in which a given member, component or structure is to be moved in a controlled manner.

BACKGROUND OF THE INVENTION

In the disclosure of the present invention reference is mostly made to the treatment of diabetes by injection or infusion of insulin, however, this is only an exemplary use of the present invention.

Portable drug delivery devices for delivering a drug to a patient are well known and generally comprise a reservoir adapted to contain a liquid drug and having an outlet in fluid communication with a transcutaneous access device such as a hollow infusion needle or a cannula, as well as expelling means for expelling a drug out of the reservoir and through the skin of the subject via the access device. Such drug delivery devices are often termed infusion pumps.

Basically, infusion pumps can be divided into two classes. The first class comprises infusion pumps which are relatively expensive pumps intended for 3-4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniencies, e.g. the pump may be prefilled thus avoiding the need for filling or refilling a drug reservoir. Examples of this type of infusion devices are known from U.S. Pat. Nos. 4,340,048 and 4,552,561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also known as a bleeding hole pump)), U.S. Pat. No. 5,527,288 (based on a gas generating pump), or U.S. Pat. No. 5,814,020 (based on a swellable gel) which all in the last decades have been proposed for use in inexpensive, primarily disposable drug infusion devices, the cited documents being incorporated by reference.

As the membrane pump can be used as a metering pump (i.e. each actuation (or stroke) of the pump results in movement of a specific amount of fluid being pumped from the pump inlet to the pump outlet side) a small membrane pump would be suitable for providing both a basal drug flow rate (i.e. providing a stroke at predetermined intervals) as well as a drug bolus infusion (i.e. a given number of strokes) in a drug delivery device of the above-described type.

More specifically, a metering membrane pump may function as follows. In an initial condition the pump membrane is located at an initial predefined position and the inlet and outlet valves are in their closed position. When the means for moving the membrane (i.e. the membrane actuator) is energized an increase of the pressure inside the pumping chamber occurs, which causes opening of the outlet valve. The fluid contained in the pumping chamber is then expelled through the outflow channel by the displacement of the pump membrane from its initial position towards a fully actuated position corresponding to the end position for the "out-stroke" or "expelling-stroke". During this phase, the inlet valve is maintained closed by the pressure prevailing in the pumping chamber. When the pump membrane is returned to its initial position (either due to its elastic properties or by means of the membrane actuator) the pressure in the pumping chamber decreases. This causes closing of the outlet valve and opening of the inlet valve. The fluid is then sucked into the pumping chamber through the inflow channel, owing to the displacement of the pump membrane from the actuated position to the initial position corresponding to the end position for the "in-stroke" or "suction-stroke". As normally passive valves are used, the actual design of the valve will determine the sensitivity to external conditions (e.g. back pressure) as well as the opening and closing characteristics thereof, typically resulting in a compromise between the desire to have a low opening pressure and a minimum of backflow. As also appears, a metering membrane functions as any conventional type of membrane pump, for example described for use as a fuel pump in U.S. Pat. No. 2,980,032.

As follows from the above, the precision of a metering pump is to a large degree determined by the pump membranes movement between its initial and actuated positions. These positions may be determined by the pump cavity in which the pump membrane is arranged, i.e. the membrane is moved between contact with two opposed surfaces, this allowing e.g. the pump to be driven by an expanding gas (see PCT/DK03/00628), or they may be determined by a membrane actuator member being moved between predefined positions. Indeed, to secure a high delivery precision it would be desirable to monitor that the pump membrane is actually moved between its two positions. Membrane movement may be measured using any convenient means such as electrical contacts or electrical impedance measurement (resistance or capacitance) between electrical contacts/elements arranged on opposed surfaces of the pump membrane and the pump housing.

Instead of, or in addition to, monitoring the pump per se it is also possible to positively detect the flow rate from any given type of pump by incorporating additional metering means, e.g. based on thermo-dilution as disclosed in EP 1 177 802.

To further monitor proper functioning of an actuated system such as a drug infusion pump, it would be desirable to provide means for detecting different operational conditions of the system, such as an occlusion condition downstream of a pump, e.g. full or partial occlusion of a transcutaneous access device. As the outlet conduit leading from the pump outlet to the distal outlet opening of a transcutaneous access device is relatively stiff, a given pressure rise in the outlet conduit during pump actuation can normally be taken as an indication for an occlusion condition and thus be utilized to detect the latter. For example, US 2003/167035 discloses a delivery device comprising pressure sensors being actuated by a resilient diaphragm arranged in flow communication with in the outlet conduit.

Having regard to the above-identified problems, it is an object of the present invention to provide an actuator system, or component thereof, suitable for driving an actuatable structure or component.

It is a further object to provide an actuator system which allows for detection of different operational conditions of the system, thereby ideally providing a system which can be actuated and controlled in a safe and efficient manner.

It is a further object to provide an actuator system which can be used in combination with a pump assembly arranged in a portable drug delivery device, system or a component therefore, thereby providing controlled infusion of a drug to a subject.

It is a further object to provide an actuator system which can be used in combination with a pump such as a membrane pump.

It is a further object of the invention to provide an actuator, or component thereof, which can be provided and applied in a cost-effective manner.

DISCLOSURE OF THE INVENTION

In the disclosure of the present invention, embodiments and aspects will be described which will address one or more of the above objects or which will address objects apparent from the below disclosure as well as from the description of exemplary embodiments.

According to a first aspect of the invention, an actuator system is provided comprising an actuator lever, a supporting structure, a moveable structure moveable by actuation of the actuator lever, and an actuator for moving the actuator lever. A first stationary pivoting joint (in the following the term pivot joint may be used as an equivalent term) is formed between the actuator lever and the supporting structure, and a second floating pivoting joint is formed between the actuator lever and the moveable structure allowing the moveable structure to float relative to the actuator lever, the floating pivoting point providing a constant-length actuator arm defined between the first pivoting joint and the second pivoting joint. By this arrangement the lever is attached to the supporting structure, however, as the joint between the lever and the moveable structure is floating, the moveable structure is allowed (to a certain degree) to move relative to the supporting structure (and visa versa) yet still preserving the arm length and thus the ability to actuate a structure in a controlled and efficient manner.

In an embodiment thereof an actuator system is provided comprising an actuator lever, a supporting structure, a moveable structure being moveable by actuation of the actuator lever, and an actuator providing an actuation force at an actuator position on the actuator lever. A first stationary pivoting joint is formed between the actuator lever and the supporting structure, whereby a first actuator arm length is defined between the first pivoting joint and the actuator position. A second floating pivoting joint is formed between the actuator lever and the moveable structure allowing the moveable structure to float relative to the actuator lever, whereby the floating pivoting point provides a second constant-length actuator arm being defined between the first pivoting joint and the second pivoting joint.

In an alternative configuration an actuator system is provided comprising an actuator lever, a supporting structure, a moveable structure moveable by actuation of the actuator lever, and an actuator for moving the actuator lever. A first floating pivoting joint is formed between the actuator lever and the supporting structure allowing the actuator lever to float relative to the supporting structure, and a second floating pivoting joint is formed between the actuator lever and the moveable structure allowing the actuator lever to float relative to the moveable structure, the floating pivoting points providing a constant-length actuator arm being defined between the first pivoting joint and the second pivoting joint. By this arrangement the lever is allowed (to a certain degree) to move relative to the supporting structure as well as the actuated structure yet still preserving the arm lengths.

In an embodiment thereof an actuator system is provided comprising an actuator lever, a supporting structure, a moveable structure being moveable by actuation of the actuator lever, and an actuator providing an actuation force at a predefined actuator position on the actuator lever. A first floating pivoting joint is formed between the actuator lever and the supporting structure allowing the actuator lever to float relative to the supporting structure, whereby a first constant-length actuator arm is defined between the first pivoting joint and the actuator position. A second floating pivoting joint is formed between the actuator lever and the moveable structure allowing the actuator lever to float relative to the moveable structure, whereby the floating pivoting point provides a second constant-length actuator arm defined between the first pivoting joint and the second pivoting joint.

For both alternatives the second joint may be arranged between the first joint and the actuator position, or the first joint may be arranged between the second joint and the actuator position.

The floating joints are advantageously formed by a line bearing (e.g. formed by a knife-edge or rounded rod member) or point bearing (e.g. formed from a pointed member or a ball) formed on the actuator lever cooperating with a substantially planar surface allowing the knife-edge or ball bearing to float relative thereto. In the present context such a planar surface would also include a groove in which a point formed member would be allowed to float. By this arrangement the actual position of a floating joint will be determined by the position of the knife-edge or ball bearing and thus by the lever, the planar surface of the other structure being allowed to move without changing the length of the lever arms.

To hold the contact structures of the joints (especially the floating joints) in contact with each other, a biasing member may be provided. As an example, the actuator may be of the coil-magnet type, the coil and magnet(s) being arranged on the actuator lever respectively the supporting structure. As long as the magnetic relationship is substantially constant (e.g. the coil is positioned within a (near) constant magnet field, the force provided by the moving component (i.e. arranged on the lever) will substantially constant.

In an exemplary embodiment the actuator system is provided in combination with a pump for pumping a liquid between an inlet and an outlet thereof, the pump comprising a pump member performing a pump stroke when actuated by the actuator lever. The pump may comprise inlet and outlet valves associated with the pump inlet respectively the pump outlet, and a pump chamber in which the pump member is moved to perform a pump stroke respectively a suction stroke. The combination may further comprise a reservoir adapted to contain a fluid drug and comprising an outlet in fluid communication with or being adapted to be arranged in fluid communication with the pump inlet, and a transcutaneous access device comprising a distal end adapted to be inserted through the skin of a subject, the transcutaneous access device comprising an inlet in fluid communication with or being adapted to be arranged in fluid communication with the pump outlet, the combination thereby providing a drug delivery device. The reservoir may be any suitable structure adapted to hold an amount of a fluid drug, e.g. a hard reservoir, a flexible reservoir, a distensible or elastic reservoir. The reservoir may e.g. be prefilled, user fillable or in the form of a replaceable cartridge which again may be prefilled or fillable.

When actuating a given member, it would be desirable to provide an actuator system which allows for detection of different operational conditions of the system, thereby ideally providing a system which can be actuated and controlled in a safe and efficient manner.

Correspondingly, according to a further aspect of the invention, an actuator system is provided comprising an actuator member for moving a structure, the actuator member having a first position and a second position, and actuating means for moving the actuator member between the first and second positions. The system further comprises detection means for detecting the first respectively the second position and supplying signals indicative thereof (e.g. when a position was reached or left), and a controller for determining on the basis of the supplied signals the time lapsed when the actuator member is moved between the first and second positions in a given direction, e.g. T-in or T-out for a suction respectively an expelling pump stroke. The controller is provided with information representing at least one defined time range, each time range being associated with movement of the actuator member in a given direction between the first and second positions and a given actuation force, e.g. as determined by a supplied current, the controller being adapted to compare the determined time lapsed with the one or more defined time ranges and perform an action corresponding to the time range associated with the determined time lapsed.

The time range(s) may be predefined, selectable or they may be dynamically influenced by actuation history over a short or long period of time. The time range(s) may be closed, open or open-ended. The action may be in the form of a "positive" action, e.g. actuating an alarm, initiating a modified actuation pattern, or a "negative" action, e.g. no action. The motion provided by the actuator may be e.g. reciprocating, linear or rotational, which movement may then be transformed into the desired actuation pattern for a given structure to be moved. Correspondingly, the actuator means may be of any suitable type, e.g. a coil-magnet system, a shape memory alloy (SMA) actuator, a solenoid, a motor, a gas generator, a piezo actuator, a thermo-pneumatic actuator, or a pneumatic actuator.

In the context of the present application and as used in the specification and claims, the term controller covers any combination of electronic circuitry suitable for providing the specified functionality, e.g. processing data and controlling memory as well as all connected input and output devices. The controller may comprise one or more processors or CPUs which may be supplemented by additional devices for support or control functions. For example, the detection means, a transmitter, or a receiver may be fully or partly integrated with the controller, or may be provided by individual units. Each of the components making up the controller circuitry may be special purpose or general purpose devices. The detection means may comprise a "sensor" per se, e.g. in the form of an electrical contact, or an optical or magnetic sensor capable of being influenced by the position of the actuator member, in combination with circuitry supplying time signals indicative of when a position was reached or left. Such circuitry may be formed fully or partly integrally with the controller. For example, both may rely on a common clock circuit. As appears, the distinction between the detection means and the controller may be more functional rather than structural.

As appears, for each direction and each force a number of defined time ranges may be provided, however, in the simplest form only a single time range associated with movement of the actuator in one direction is provided. For example, a determined time lapsed within such a single time range may indicate an alarm or malfunctioning condition whereas lapsed times outside this range would be considered within normal operation. In a more advanced form a number of time ranges is provided for each direction. The time ranges may be "closed" (e.g. 50-100 ms) or "open" (e.g. >50 ms or <100 ms).

As appears, it is important that a determined lapsed time is correctly correlated with a given actuator movement. Thus, in an exemplary embodiment the controller is adapted to control the actuating means for moving the actuator between the first and second positions in a given direction, and determine a lapsed time corresponding to a given actuation of the actuator member between the first and second positions in a given direction. However, a given actuator movement may also be "passive", i.e. provided by forces not "actively" generated by actuator means. For example, an actuated movement may be followed immediately by a passive movement (e.g. provided by an elastic member deformed during the active movement, the elastic member then serving as an actuator) which could then be correlated to the former.

To further control the relation between movement and time, the controller may be adapted to determine on the basis of signals supplied by the detection means that the actuator is correctly positioned in either the first or the second position corresponding to the given direction of actuation, and provide a signal (e.g. error or alarm signal) in case the actuator member is not correctly positioned corresponding to the given direction of actuation.

To provide time signals well correlated to the first and second positions, an exemplary embodiment of the system comprises first and second stop means adapted to engage the actuator member in the first respectively the second position, whereby engagement between the actuator member and the first respectively the second stop means allows the detection means to detect that the actuator member is in the first respectively the second position. It should be emphasized that the term "actuator member" in this context may be a structure of the actuator member per se (e.g. an actuator lever) or a component functionally and motionally coupled to the actuator member (e.g. a component moved by the actuator such as a piston or a pump membrane) such that the first and second positions for such a component correspond to the first and second positions for the actuator member per se. Detection of the "stop" positions may be by any suitable detection means, e.g. comprising electrical contacts, optical or magnetic sensors.

As stated above, the time range(s) may be predefined, selectable or they may be dynamically determined. For example, upon initial use of a given actuated system, the system may be actuated a number of times (e.g. when priming a pump), and the lapsed times detected during these actuations be used to determine a value which is unique for the actual system, which value may then be used to calculate one or more defined ranges to be used for the subsequent determination of different conditions for the system. As a safety feature, the actuator system may be provided with preset values or ranges within which the dynamically determined ranges should fall, this to prevent that a dynamic range is determined for a defective system.

As stated in the introductory portion, the actuator system of the present invention may find broad application in any field in which a given member, component or structure is to be moved in a controlled manner. In an exemplary embodiment the actuator system is provided in combination with a pump for pumping a liquid between an inlet and an outlet thereof, the pump comprising a pump member performing a pump action when actuated by the actuator member moved between the first and second positions. The pump may be of any desired type, e.g. a membrane pump, a piston-cylinder pump or a roller-tube pump. The actuator system of the present invention may be used to monitor and detect normal operations of the system as well as operations associated with a malfunctioning of the system or the application in which a given pump is used.

For example, the pump outlet of a drug delivery device may be in fluid communication with a hydraulically rigid outlet conduit, such that a partial or full occlusion of the outlet conduit (e.g. corresponding to a distal outlet opening of conduit such as a distal opening of a cannula or a hollow needle) will result in a substantially unrestricted pressure rise in the outlet conduit, whereby for a predetermined actuation force applied to the pump member from the actuation member the duration of the pump stroke will be extended. To detect such a condition the controller is provided with information representing a defined time range indicative of an occlusion condition in the outlet conduit, the controller being adapted to produce an alarm signal in case the determined lapsed time of a pump stroke is within the occlusion condition time range. The alarm signal may be used to activate an associated user alarm such as an audible, visual or tactile alarm, or it may be used to initially try to overcome the occlusion by modifying pump operation.

The pump may comprise inlet and outlet valves associated with the pump inlet respectively the pump outlet, and a pump chamber in which the pump member is moved to perform a pump stroke respectively a suction stroke, the suction stroke being associated with the actuator member being moved between the second and first positions. For such a combination the controller may comprise information representing one or more of the following defined time ranges for a given actuation force and/or direction: (a) a time range associated with normal pump operation during a pump stroke, (b) a time range associated with a shortened pump stroke, (c) a time range associated with a prolonged pump stroke, (d) a time range associated with normal pump operation during a suction stroke, (e) a time range associated with a shortened suction stroke, and (f) a time range associated with a prolonged suction stroke, where the controller being adapted to compare the determined time lapsed with the defined time range(s) and perform an action corresponding to the time range associated with the determined time lapsed. Depending on the state of the pump a given time range may define different conditions, e.g. during priming of the pump and during normal operation of the pump, a given range may correlate to different situations. Further time ranges may be defined based upon the above time ranges, e.g. for each time range a lower and an upper time range may be defined, or the different time ranges may be used to calculate combined time ranges, e.g. a sum or difference of two ranges or an average of two ranges.

Such a combination may further comprise a reservoir adapted to contain a fluid drug, the reservoir comprising an outlet in fluid communication with, or being adapted to be arranged in fluid communication with, the pump inlet. The combination may further comprise a transcutaneous access device comprising a pointed end adapted to penetrate the skin of a subject, the access device comprising an inlet in fluid communication with, or being adapted to be arranged in fluid communication with, the pump outlet. For such a device the different time ranges (a)-(f) may be used to detect different conditions during operation of the pump. For example, (a) may be used to indicate normal pump operation, (b) to indicate that air is pumped instead of liquid, e.g. during priming of the pump or when the pump is sucking air due to a leak, or that the inlet valve is malfunctioning (c) to indicate a further occlusion situation, e.g. more severe, (d) to indicate normal pump chamber filling during operation, (e) to indicate inlet valve malfunctioning, and (f) to indicate that a non-vented reservoir is close to empty. As indicated, the time ranges are associated with a given actuation force, such that it may be necessary to have two or more sets of ranges if it is desirable to operate the actuation means at different levels. For example, a coil-magnet actuator may be operated at different current levels, e.g. 1V, 2V and 3V dependent upon the operational requirements. The actuator may start operate e.g. a pump at 1V and if an occlusion situation is detected, the current may be raised to overcome the obstruction. Indeed, for such a higher current a different set of time ranges will be relevant.

The present invention also provides a method for operating a pump having a moveable pump member, comprising the steps of (i) actuating the pump member between first and second positions, (ii) determining the time lapsed when the pump member is moved between the first and second positions in a given direction and under given conditions, (iii) comparing the determined time lapsed with one or more defined time ranges, and (iv) performing an action corresponding to the time range associated with the determined time lapsed. One or more time ranges may either be predetermined or calculated on basis of previously determined times lapsed. The pump may comprise an inlet in fluid communication with a liquid filled reservoir, and an outlet in fluid communication with a transcutaneous access device, wherein the defined time range(s) is/are associated with one or more of the following conditions, an empty or near-empty reservoir, pumping of air, pumping of liquid, obstruction of the inlet, obstruction of the outlet, obstruction of the transcutaneous access device, and pump malfunctioning.

The invention also provides a method of controlling an actuator member, comprising the steps of (i) providing an actuator member suitable for moving a structure, the actuator member having a first position and a second position, (ii) providing an actuator for moving the actuator member between the first and second positions, (iii) providing a detector for detecting the first respectively the second position and supplying time signals indicative thereof, (iv) providing a controller comprising information representing at least one defined time range, each time range being associated with movement of the actuator member in a given direction between the first and second positions and a given actuation force, (v) actuating the actuator to thereby move the actuation member, (vi) supplying time signals to the controller, (vii) determining on the basis of supplied time signals the time lapsed when the actuator member is moved between the first and second positions in a given direction, (viii) comparing the determined time lapsed with one or more defined time ranges, and (ix) performing a control action corresponding to the time range associated with the determined time lapsed.

For many mechanical systems static frictional forces will be relevant. If this is the case in a given system operated by the above-described actuator system, it may be desirable to "ramp up" the actuation force to thereby prevent "overshoot"

and thereby too fast movement between the two positions which would render it more difficult to discriminate between different conditions.

A further strategy to detect an occlusion situation for a pump is based on the principle of detecting the force (or a value representative thereof) necessary to move the pump actuator away from the first (i.e. initial) position. By slowly ramping up the force (e.g. current through a coil) it will be possible to detect the force necessary to overcome a static friction force as well as the pressure in the system. In this way the current may be utilized to detect an occlusion situation. Further, when an initially empty pump is primed, air is pumped having a very low viscosity which can be used to detect properties of the pump system, e.g. static friction and elastic properties of a pump membrane. For example, when the pump is primed the energy necessary for driving the pump membrane between its initial and actuated positions can be determined. When subsequently the energy necessary for driving the pump membrane between its initial and actuated positions when liquid is pumped is determined, the difference between the energies can be used to calculate the energy used for the pump work and thus the pressure in the pump system. When liquid is pumped under normal operation conditions, pump actuation may be controlled to achieve pump time cycles under which the pump operates most efficiently, e.g. to ensure that the valves operate efficiently with minimum backflow.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals (including peptides, proteins, and hormones), biologically derived or active agents, hormonal and gene based agents, nutritional formulas and other substances in both solid (dispensed) and liquid form. In the description of the exemplary embodiments reference will be made to the use of insulin. Correspondingly, the term "subcutaneous" infusion is meant to encompass any method of parenteral delivery to a subject.

BRIEF DESCRIPTION OF THE DRAWINGS

In the following the invention will be further described with references to the drawings, wherein.

In the figures like reference numerals are used to mainly denote like or similar structures.

DESCRIPTION OF EXEMPLARY EMBODIMENTS

Figure 1:
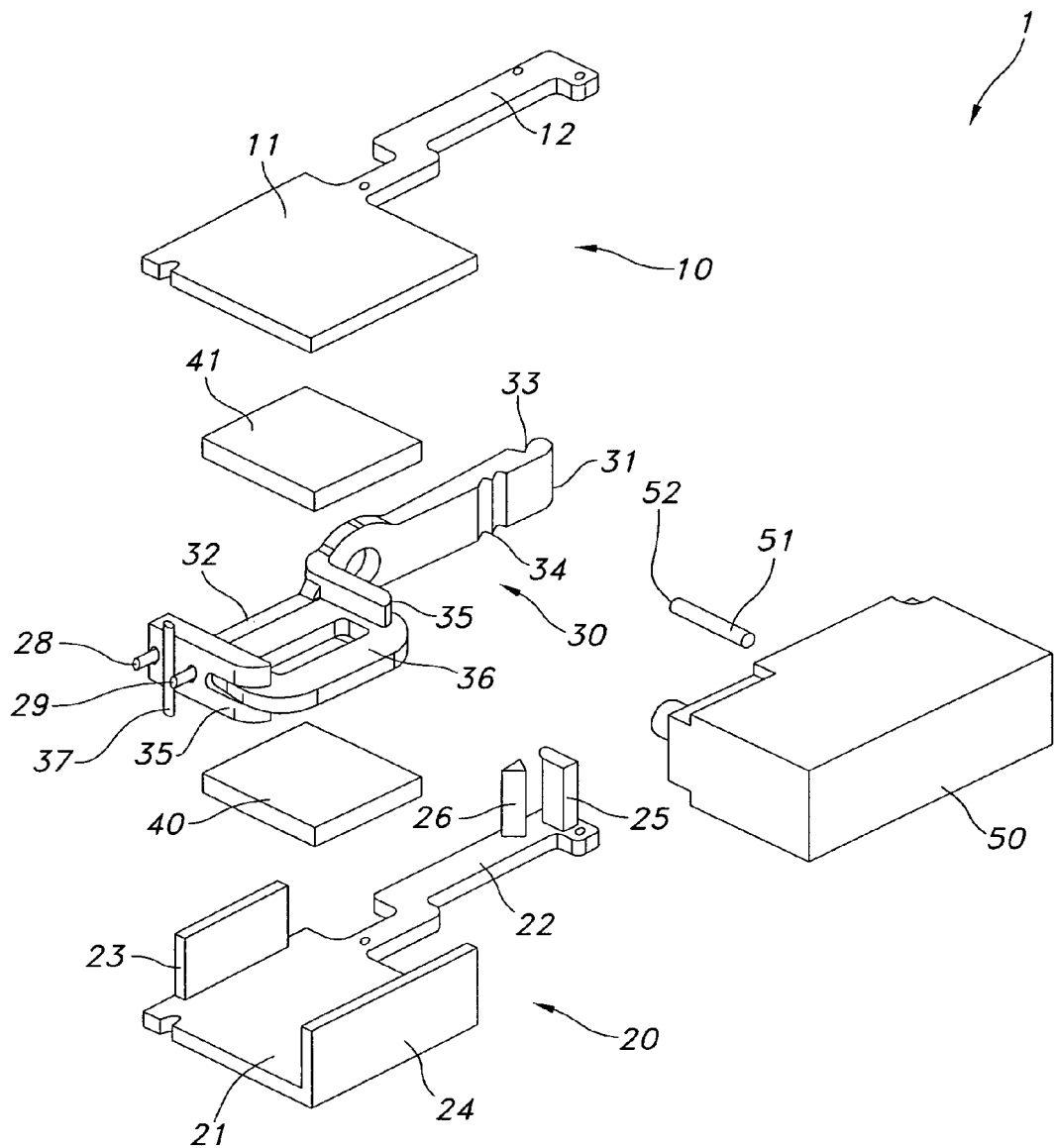
FIG. 1 shows exploded view of a first embodiment of an actuator and a first embodiment of a pump and actuator assembly

When in the following terms as "upper" and "lower", "right" and "left", "horizontal" and "vertical" or similar relative expressions are used, these only refer to the appended figures and not to an actual situation of use. The shown figures are schematic representations for which reason the configuration of the different structures as well as their relative dimensions are intended to serve illustrative purposes only.

More specifically, a pump actuator 1 comprises an upper housing member 10 and a lower housing member 20, both comprising a distal main portion 11, 21 and a therefrom extending proximal arm portion 12, 22. On an upper surface of the lower main portion a pair of opposed walls 23, 24 are arranged and at the proximal end of the lower arm a post member 25 and a knife-edge member 26 are arranged perpendicularly to the general plane of the lower arm. In an assembled state the two main portions form a housing in which a pair of magnets 40, 41 is arranged on the opposed upper and lower inner surfaces of the main portions. The pump actuator further comprises a lever 30 having a proximal end 31 comprising first and second longitudinally offset and opposed joint structures in the form of a groove 33 and a knife-edge 34 arranged perpendicular to a longitudinal axis of the lever, and a distal end 32 with a pair of gripping arms 35 for holding a coil member 36 wound from a conductor. A membrane pump is arranged in a pump housing 50 having a bore in which an actuation/piston rod 51 is arranged, the rod serving to actuate the pump membrane of the membrane pump (see below for a more detailed description of the membrane pump). The outer free end of the rod is configured as a substantially planar surface 52. In an assembled state the lever is arranged inside the housing with the coil positioned between the two magnets, and the housing is attached to the pump housing with the knife-edge of the knife-edge member 26 nested in the lever groove 33 and the knife-edge of the lever is positioned on the planar rod end surface, this arrangement providing first and second pivoting joints. As the actuating rod is biased outwardly by the elastic pump membrane the lever is held in place by the two joints and the housing in combination, the lever only being allowed to pivot relative to the first joint (see also below). Due to this arrangement a gearing of the force provided from the coil-magnet actuator to the actuation rod is realized, the gearing being determined by the distance between the two pivoting joints (i.e. a first actuator arm) and the distance between the first/proximal pivoting joint and the "effective" position of the coil on the lever (i.e.

a second actuator arm). By the term "effective", the issue is addressed that the force generated by the coil actuator may vary as a function of the rotational position of the lever, this being due to the fact that the coil is moved between stationary magnets, which may result in a varying magnetic field for the coil as it is moved. The actuator further comprises a pair of contact members 28, 29 adapted to cooperate with a contact rod 37 mounted in the housing and which will be described with reference to FIG. 3A.

Figure 2A:
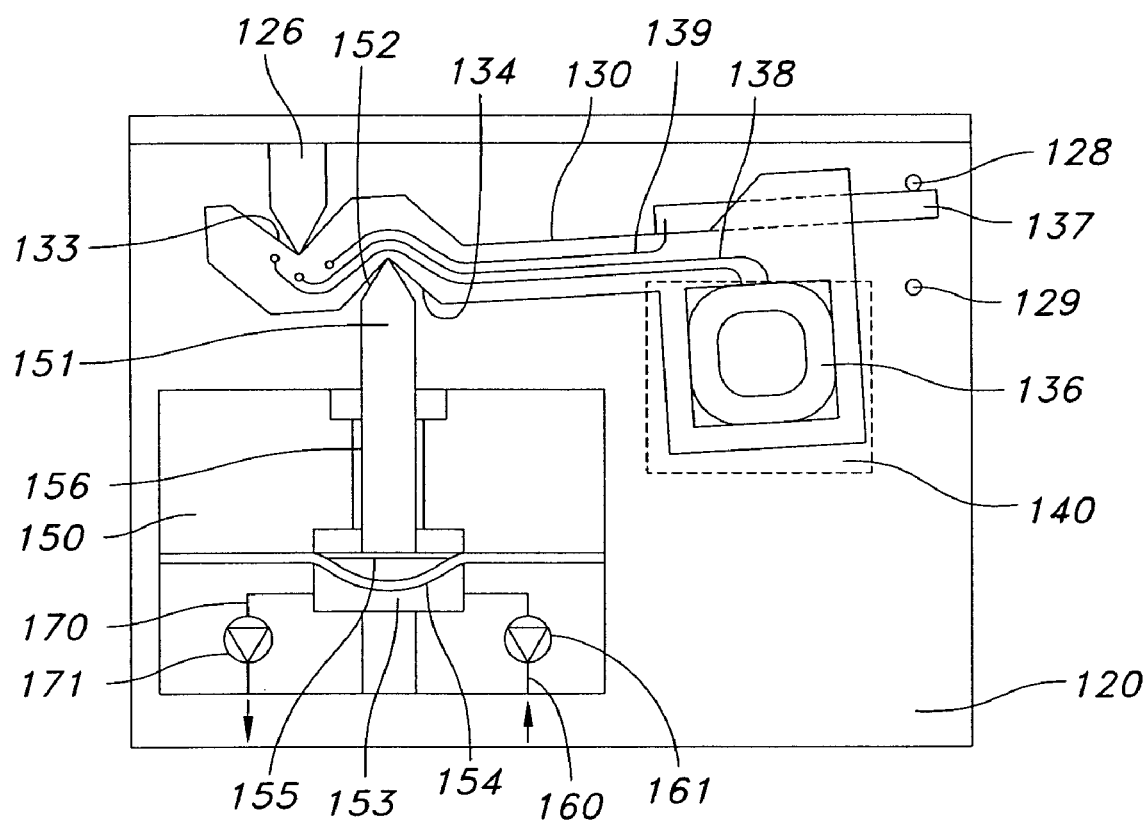
FIGS. 2A-2C show schematic cross-sectional views through a second embodiment of a pump and actuator assembly in different stages of actuation
Figure 2B:
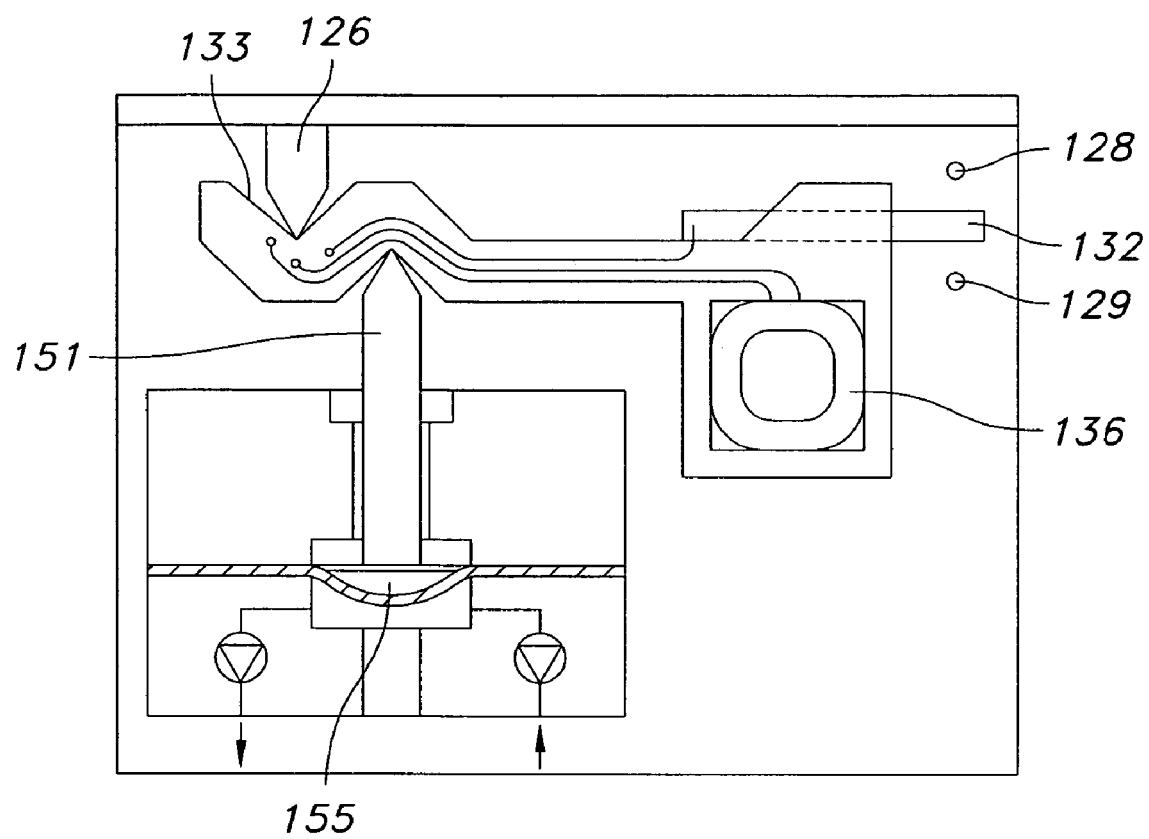
Figure 2C:
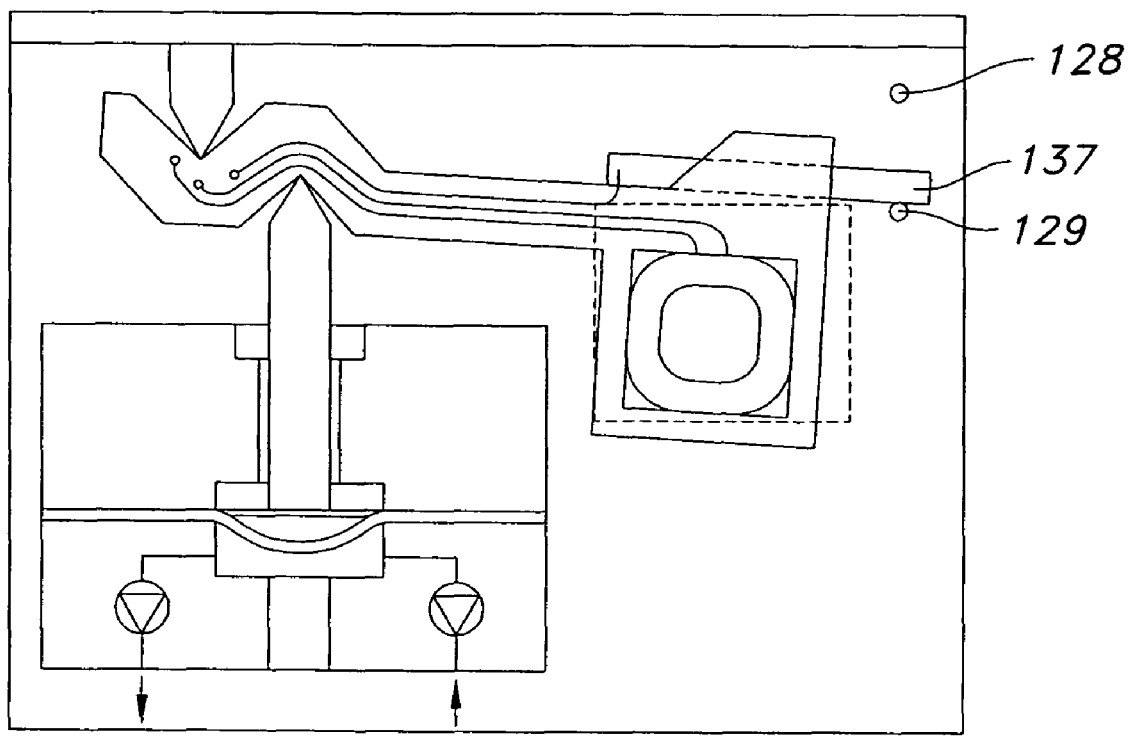

FIGS. 2A-2C show schematic cross-sectional views through a second embodiment of a pump and actuator assembly for a pump actuator of the type shown in FIG. 1, the sections corresponding to a plane above the lever. Corresponding to the FIG. 1 embodiment, the assembly comprises a housing 120 for accommodating the actuator lever 130, a pair of magnets 140 as well as a pump assembly 150, the housing comprising a knife-edge member 126. The pump assembly may be of the type disclosed in FIGS. 11-16. The actuator lever comprises first and second grooves 133, 134, a coil 136 and a contact rod 137 adapted to engage first and second contact members 128, 129 arranged on the housing. The lever further comprises a pair of conductors 138 for energizing the coil as well as a conductor 139 for the contact rod. In the shown embodiment the conductors are shown with terminal contact points, however, advantageously the three conductors are formed on a flex-print attached to the lever and connected to a structure of the device in which the actuator is mounted, the connection between the moving lever and the other structure being provided by a film hinge formed by the flex-print. The pump comprises a pump chamber 153, in which an elastic pump membrane 154 is arranged, and a bore 156 for slidingly receive and support a piston rod 151 with a convex piston head 155 engaging the pump membrane. The pump membrane is in all positions in a stretched state, the membrane thereby exerting a biasing force on the piston rod which is used to hold the actuator lever in place as described above. The pump further comprises an inlet conduit 160 with an inlet valve 161 in fluid communication with the pump chamber, and an outlet conduit 170 with an outlet valve 171 in fluid communication with the pump chamber. The valves may be of any desirable configuration, but advantageously they are passive membrane valves.

FIG. 2A shows the pump and actuator assembly in an initial state with the actuator lever in an initial position in which the contact rod 137 is positioned against the first contact member 128 which thereby serves as a stop for the lever. As indicated above, the piston rod 151 has a length which ensures that it is forced by the pump membrane into contact with the lever in its initial position. The terms "initial" and "actuated" state refers to the shown embodiment in which the actuator is used to actuate the pump to produce a pump stroke, however, although the suction stroke of the pump may be passive (i.e. performed by the elastic energy stored in the pump membrane during the pump stroke) the actuator may also be actuated in the reverse direction (i.e. from the actuated to the initial position) to actively drive the pump during the suction stroke. Thus, in more general terms the actuator is moved between first and second positions in either direction.

FIG. 2B shows the pump and actuator assembly in an intermediate state in which the coil 136 has been energized (e.g. by a ramped PWM pulse) pivoting the lever relative to the first pivot joint 126, 133 thereby actuating the pump membrane via the piston 151, 155. As appears, the contact rod is now positioned between the two contact members 128, 129.

FIG. 2C shows the pump and actuator assembly in a fully activated state with the actuator lever in a fully actuated position in which the contact rod 137 is positioned against the second contact member 129 which thereby also serves as a stop for the lever. In this way the stroke distance and thus the stroke volume of the pump membrane is determined by the two contact (or stop) members 128, 129. In this position the coil is de-energized and the actuator lever is returned to its initial position by means of the biasing force of the pump membrane which during its travel to its initial position performs a suction stroke. If desirable, the actuator lever may also be returned to its initial position actively by reversing the current flow in the coil, however, in order to keep the actuator rod and the lever in contact with each other, this actuation should not be too swift.

Figure 3A:
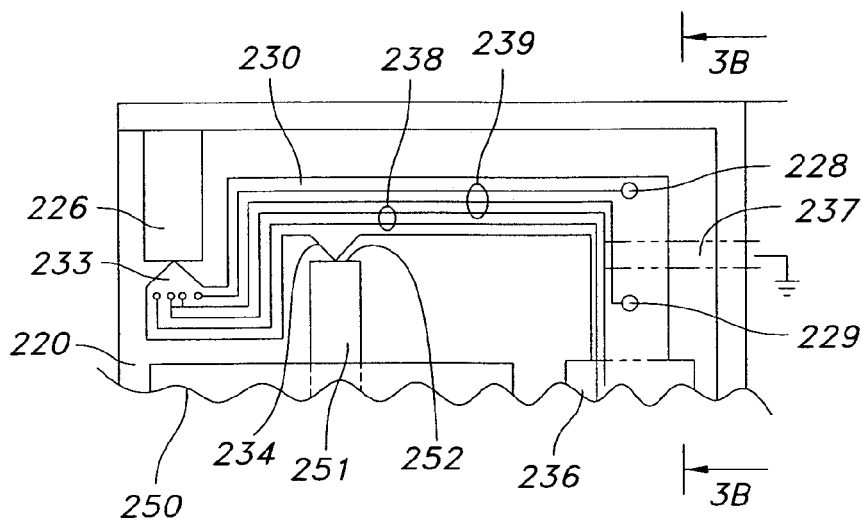
FIGS. 3A and 3B show schematic cross-sectional views through a part of a third embodiment of a pump and actuator assembly

FIG. 3A shows an alternative embodiment in which the actuator lever comprises two knife-edge members 233, 234 which cooperate with substantially planar surfaces on the housing support 226 and the free piston end 252 to provide first and second pivoting joints. By this arrangement the distance between the two pivoting points, and thus the piston stroke length, is determined by properties of the lever which is allowed to "float" with respect to the two planar joint surfaces. Indeed, the housing should be provided with appropriate stops (not shown) preventing the lever from dislocating out of engagement. Further, two contact members 228, 229 are arranged on the lever cooperating with a contact rod 237 mounted on the housing, the opposed surfaces of the rod thereby serving as first and second stop means adapted to engage the actuator member in the initial respectively the actuated position. In this way the rotational freedom of the lever relative to the first pivoting joint, and thus the piston stroke length, is determined by the position of the contact members and the diameter of the contact rod. As appears, by this arrangement the structures most important for controlling the stroke length of the piston are all provided as parts of the lever. In an alternative embodiment (corresponding to FIG. 1) the housing support 226 comprises a groove in which the first knife-edge member 233 is located. In this way the lever is no longer allowed to "float", however, due to the planer surface 252 on the piston, the stroke length is controlled by the position of the knife-edge members and not the precise position of the piston relative to the housing support groove. A non-floating joint between the housing and the lever is not limited to a knife-edge joint but may have any desirable configuration, e.g. a film hinge joint. Further, the line-contact joint provided by a knife-edge joint may be replaced by a punctual-contact joint provided by e.g. a spherical member resting on a planar surface. In the shown embodiment two pair of conductors 238, 239 are supplied to the coil respectively the contact members, however, alternatively the contact members may be connected to the coil conductors which then may serve to both energize the coil and conduct contact information to a processor or control system (not shown). For example, in case the contact rod is provided with a given resting voltage this voltage will change as the coil is energized with the contact rod in contact with the first contact member 229 and will change again as the second contact member 228 is moved into contact with the contact rod.

Figure 3B:
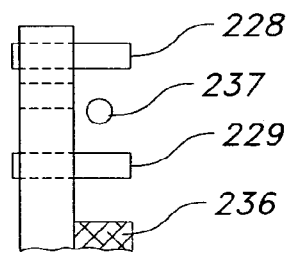

In the FIGS. 2 and 3 embodiments the piston-lever joint is provided between the housing-lever joint and the actuator coil, however, the positions may also be reversed such that the housing-lever joint is arranged between the piston-lever joint and the coil (not shown).

Figure 4:
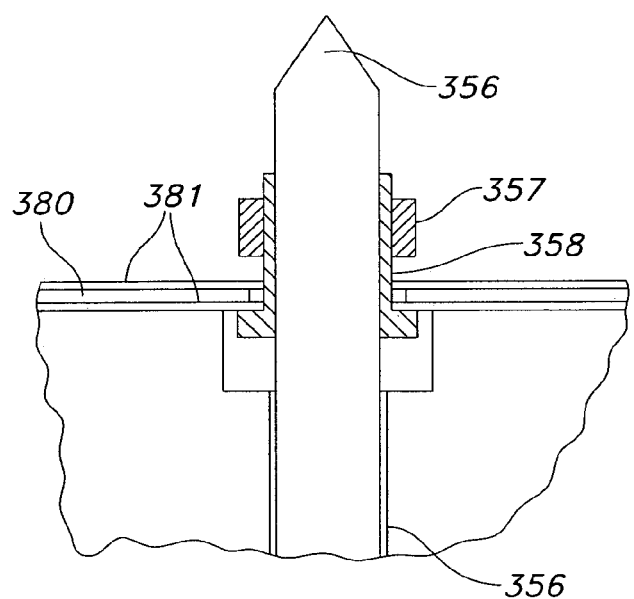
FIG. 4 shows a cross-sectional view through piston rod mounted in a pump.

In FIGS. 2 and 3 the rotational (pivoting) freedom for the actuator lever has been provided by structures associated with the lever, however, in an alternative embodiment shown in FIG. 4 the structures controlling rotational lever movement and providing contact information are associated with the piston rod. More specifically, the piston rod 356 comprises first and second collar members 358, 357 forming a gap in which a stop member 380 connected to the pump housing is arranged. In this way piston stroke length is determined by the thickness of the stop member and the distance between the two collar members. In the shown embodiment the two collar members are formed from metal and cooperate with a pair of conductors 381 arranged on the stop member.

Figure 5:
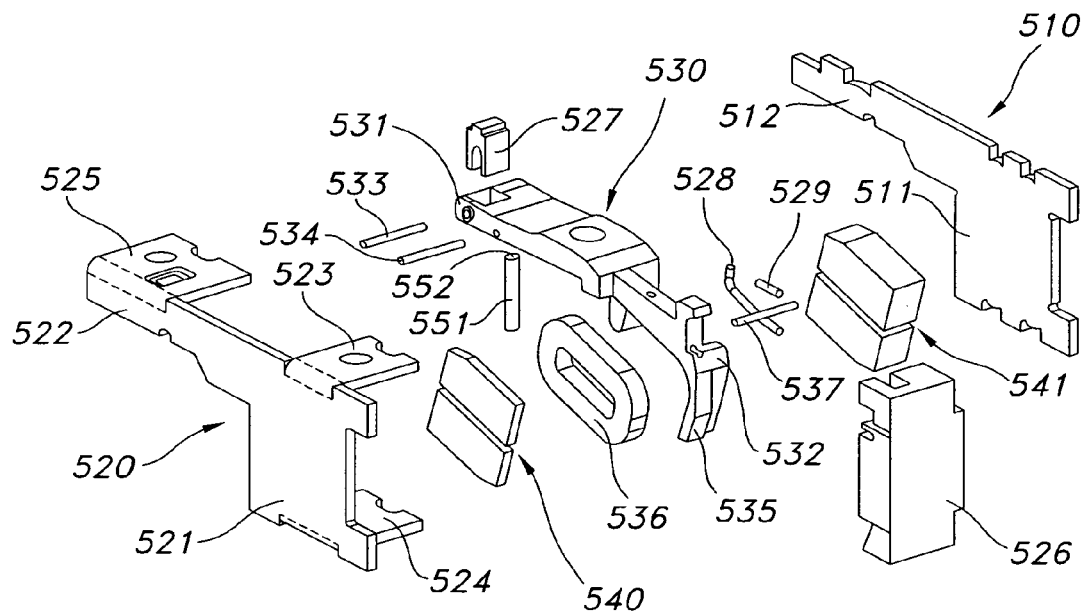
FIG. 5 shows an exploded view of a second embodiment of an actuator for a fourth embodiment of a pump and actuator assembly

With reference to FIG. 5 a further pump actuator will be described. Although the figure is oriented differently, the same terminology as for FIG. 1 will be used, the two pump actuators generally having the same configuration. The pump actuator 500 comprises an upper housing member 510 and a lower housing member 520, both comprising a distal main portion 511, 521 and a there from extending proximal arm portion 512, 522. Extending from the lower main portion a pair of opposed connection members 523, 524 are arranged, and at the proximal end of the lower arm a proximal connection member 525 is arranged perpendicularly to the general plane of the lower arm, the proximal connection member serving as a mount for a joint mount 527 comprising a slot for receiving an axle rod. Further, a separate proximal connection member 526 is provided. In an assembled state the two main portions and the proximal connection member form a housing in which two pair of magnets 540, 541 are arranged on the opposed upper and lower inner surfaces of the main portions. The pump actuator further comprises a lever 530 having a proximal end 531 comprising first and second longitudinally offset and opposed joint structures in the form of an axle rod 533 respectively a joint rod 534 arranged perpendicular to a longitudinal axis of the lever, and a distal end 532 with a pair of gripping arms 535 for holding a coil member 536 wound from a conductor. A membrane pump (not shown) comprises an actuation/piston rod 551 is arranged, the piston rod serving to actuate the pump membrane of the membrane pump. The outer free end of the rod is configured as a substantially planar surface 552. The actuator further comprises a pair of rod-formed contact members 528, 529 mounted on the distal end of the lever and adapted to cooperate with a contact rod 537 mounted in the proximal connection member. Although the two joint rods 533, 534 and the contact members 528, 529 are shown as separate members, they are preferably all metallic members moulded into a lever formed from a polymeric material.

Figure 6:
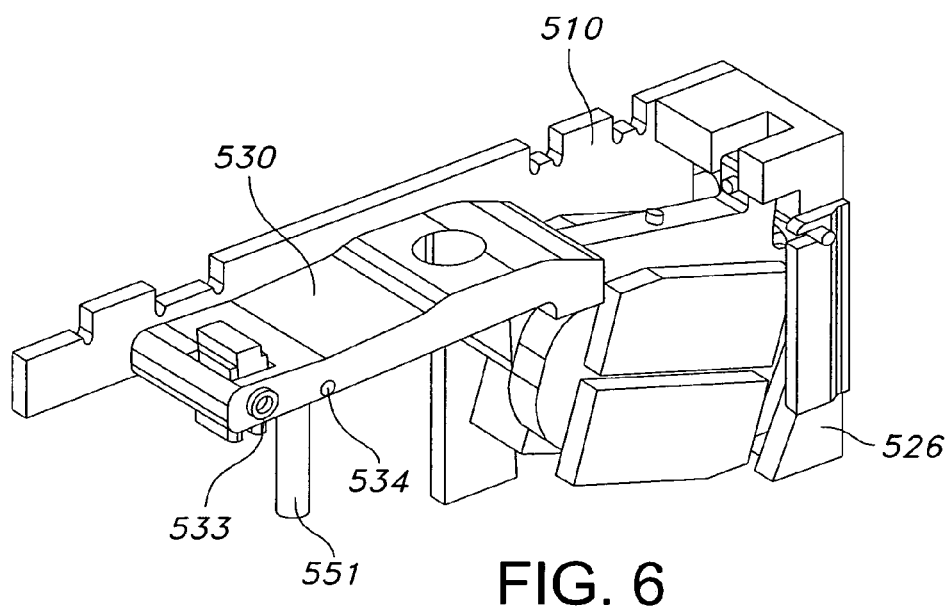
FIG. 6 shows the actuator of FIG. 5 in an assembled state.

In an assembled state as shown in FIG. 6 (the lower housing member not being shown for clarity reasons) the lever is arranged inside a housing formed by the upper and lower housing members and the proximal connection member, with the coil positioned between the two pair of magnets. The axle rod 533 is arranged in the slot of the joint mount thereby forming a proximal pivot joint. When the actuator is attached to a pump assembly (see e.g. FIG. 11) the joint rod 534 engages the substantially planar end surface 552 of the piston rod, thereby forming a distal floating knife-edge pivot joint. Although the joint rod is not a "knife", the circular cross-sectional configuration of the rod provides a line of contact between the rod and the end surface, and thus a "knife-edge" joint. Using a more generic term, such a joint may also be termed a "line" joint. Due to this arrangement a gearing of the force provided from the coil-magnet actuator to the actuation rod is realized, the gearing being determined by the distance between the two pivot joints and the distance between the proximal pivot joint and the "effective" position of the coil on the lever. As the piston rod is biased outwardly by the elastic pump membrane the lever is held in place by the two joints and the housing in combination, the lever only being allowed to pivot relative to the first joint (see also below).

Figure 7:
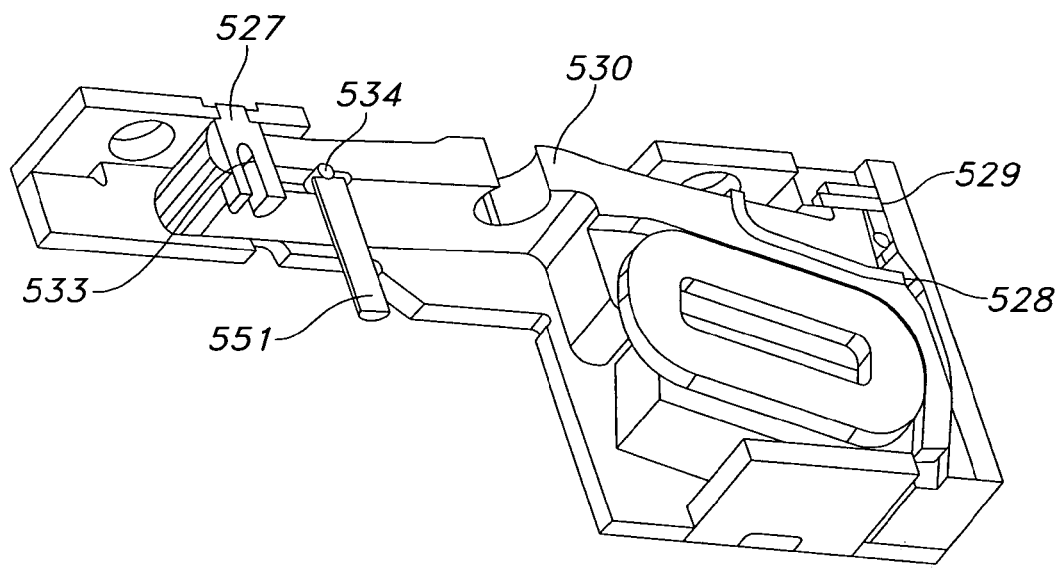
FIG. 7 shows a cross-sectional view of the actuator of FIG. 5.

In the cross-sectional view of FIG. 7 it can be seen how the axle rod 533 is arranged in the slotted joint mount 527 (e.g. by snap-action) to form a pivot joint (which in the shown configuration may also be termed a bearing), and how the joint rod 534 engages the free end of the piston rod 551 to form a floating knife-edge pivot joint. Further, the contact members 528, 529 embedded in the lever 530 can be seen.

Figure 8:
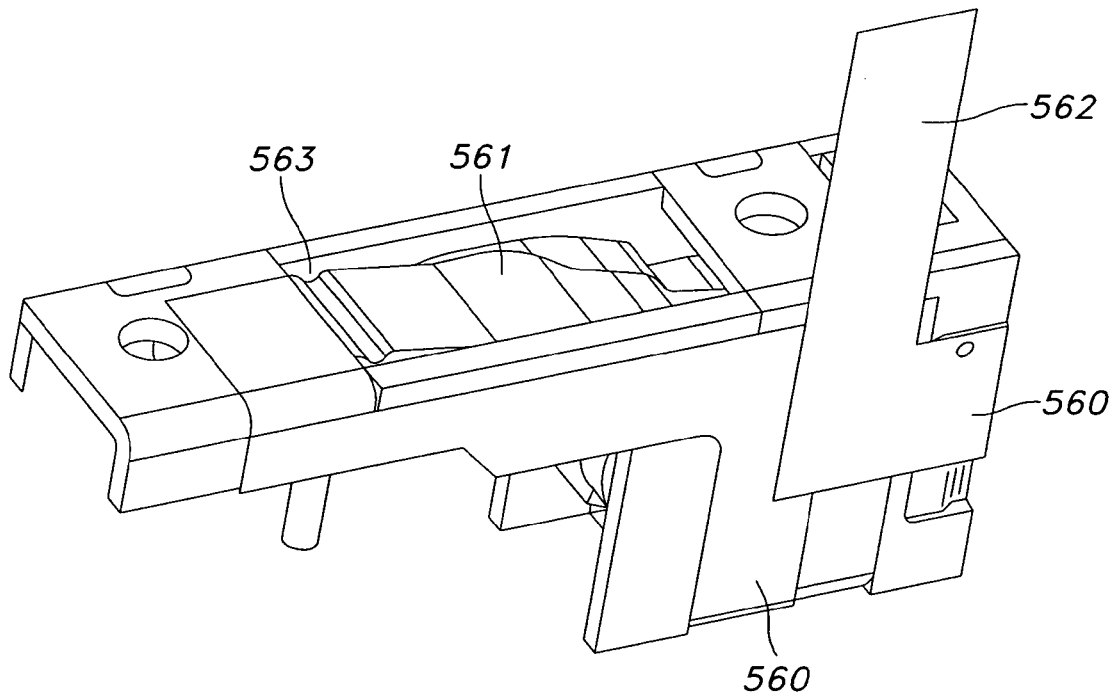
FIG. 8 shows the actuator of FIG. 5 in an assembled state with a flex print mounted.

In order to provide electrical connections between the electrical components of the actuator, i.e. the contact members and the coil, and controller circuitry (see FIG. 11) the assembled actuator is provided with a flex print as seen in FIG. 8. The flex print comprises a main portion 560 mounted to the housing of the actuator, a lever portion 561 mounted to the lever, and a connecting portion 562 providing connection with the controller electronics. A film hinge 563 is provided between the main portion and the lever portion, this allowing the lever to pivot substantially freely. The flex print may be attached by any suitable means, e.g. adhesives or mechanical connectors.

Figure 9A:
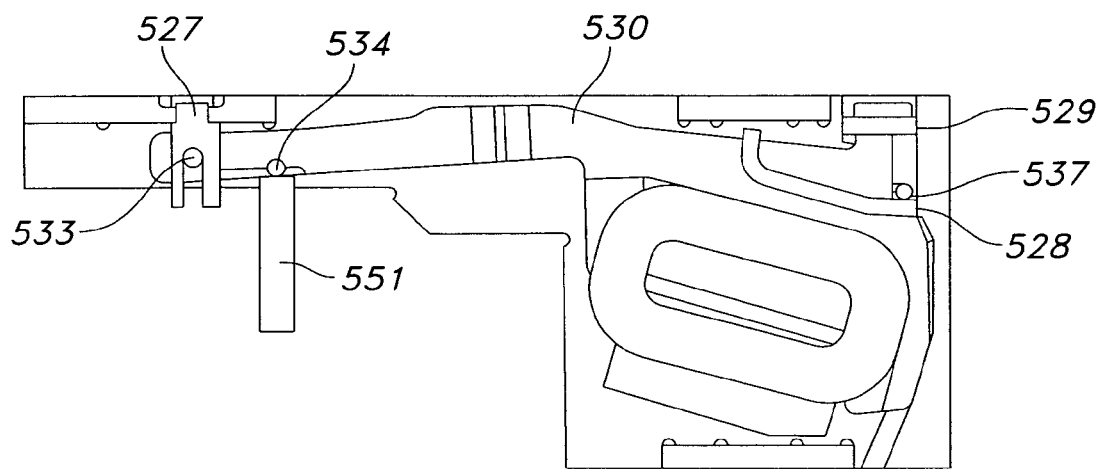
FIGS. 9A-9C show cross-sectional views through the actuator assembly of FIG. 5 in different stages of actuation.
Figure 9B:
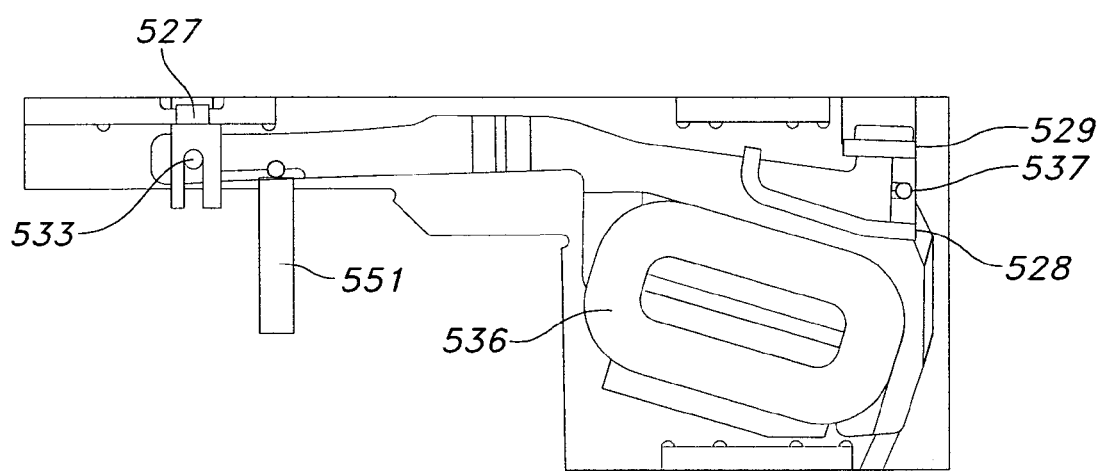
Figure 9C:
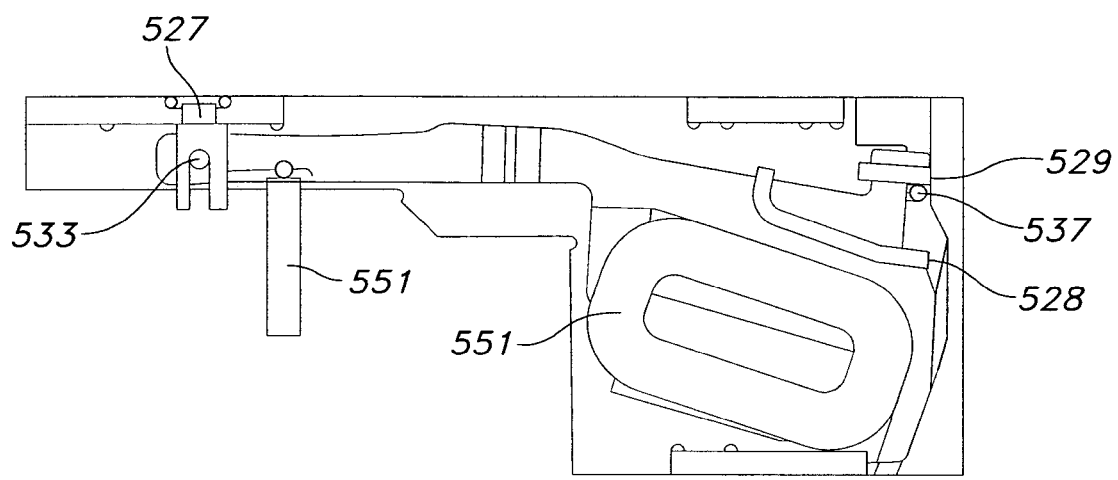

FIGS. 9A-9C show cross-sectional views through an actuator assembly of the type shown in FIG. 5, the sections corresponding to a plane through the lever. The actuator is shown in an engagement with a piston rod 551 of a membrane pump (not shown) of the same principle configuration as shown in FIG. 2A. The pump membrane is in all positions in a stretched state, the membrane thereby exerting a biasing force on the piston rod which is used to hold the actuator lever in place as described above.

FIG. 9A shows the piston rod and actuator assembly in an initial state with the actuator lever in an initial position in which the contact rod 537 is positioned against the first contact member 528 which thereby serves as a stop for the lever. A proximal non-floating pivot joint is formed between the axle rod 533 and the slotted joint mount 527, and a distal floating pivot joint is formed between the joint rod 534 and the upper end of the piston rod 551. By this arrangement the distance between the two pivot points, and thus the piston stroke length, is determined by properties of the lever, whereas the lever and the piston rod is allowed to "float" with respect to each other. Further, the two contact members 528, 529 arranged on the lever cooperate with the contact rod 537 mounted on the housing, the opposed surfaces of the rod thereby serving as first and second stop means adapted to engage the actuator member (here: the lever) in the initial respectively the actuated position. In this way the rotational freedom of the lever relative to the first pivot joint, and thus the piston stroke length, is determined by the position of the contact members and the diameter of the contact rod. As appears, by this arrangement the structures most important for controlling the stroke length of the piston are all provided as parts of the lever. As indicated above, the piston rod 551 has a length which ensures that it is forced by the pump membrane into contact with the lever in its initial position. As for the embodiment of FIGS. 3A-3C the terms "initial" and "actuated" refers to the shown embodiment in which the actuator is used to actuate the pump to produce a pump stroke.

FIG. 9B shows the actuator assembly in an intermediate state in which the coil 536 has been energized pivoting the lever relative to the proximal pivot joint 533, 527 thereby actuating the pump membrane via the piston 551. As appears, the contact rod is now positioned between the two contact members 528, 529.

FIG. 9C shows the actuator assembly in a fully activated state with the actuator lever in a fully actuated position in which the contact rod 537 is positioned against the second contact member 529 which thereby also serves as a stop for the lever. In this way the stroke distance and thus the stroke volume of the pump membrane is determined by the two contact (or stop) members 528, 529. In this position the coil is de-energized and the actuator lever is returned to its initial position by means of the biasing force of the pump membrane which during its travel to its initial position performs a suction stroke. If desirable, the actuator lever may also be returned to its initial position actively by reversing the current flow in the coil.

As appears from the above, the two contact/stop members serve to control the stroke volume of the pump, however, they may also be used to control operation and performance of the actuated component (e.g. a pump) and the system/device in which it is embedded. More specifically, such information can be retrieved by detecting the time lapsed for moving the lever between its initial and actuated position. In the following this principle will be illustrated by means of a skin-mountable drug delivery device comprising a drug-filled reservoir, a pump and a transcutaneous access device. Before turning to the control system, an illustrative drug delivery device will be described in detail.

Figure 10:
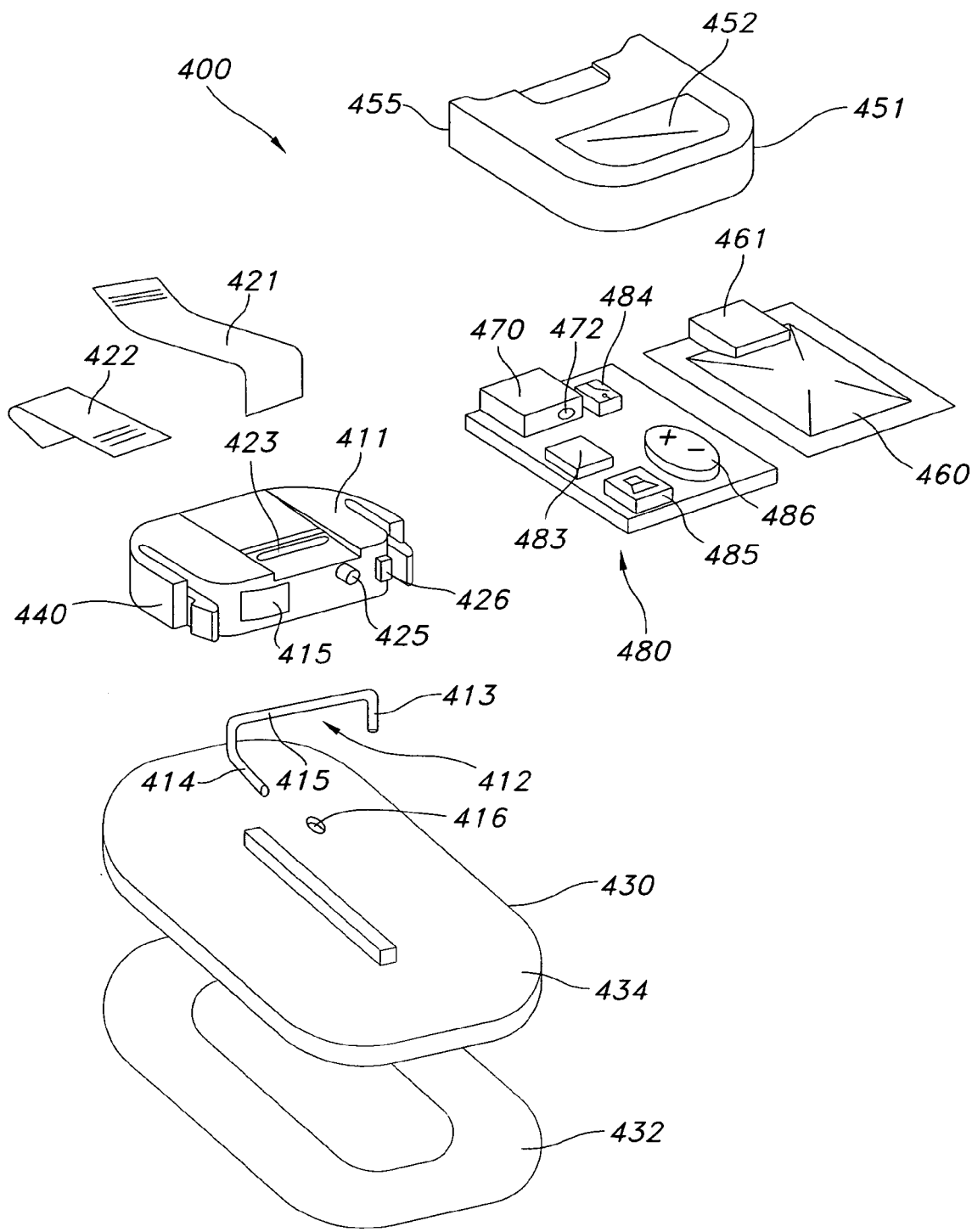
FIG. 10 shows in an exploded perspective view a drug delivery device comprising a pump and actuator assembly.

More specifically, FIG. 10 shows in an exploded perspective view a medical device in the form of a modular skin-mountable drug delivery device 400 comprising a skin-mountable patch unit 410 and a pump unit 450, this configuration allowing a pump unit to be used a number of times with a new patch unit. The drug delivery device 400 comprises a patch unit 410 having a housing 411, a base member 430 with a lower mounting surface adapted for application to the skin of a subject, an insertable transcutaneous access device in the form of a hollow infusion needle, and a separate reservoir and pump unit 450. In the shown embodiment the base member comprises a relatively rigid upper portion 431 attached to a more flexible adhesive patch member 432 provided with a gripable strip and having a lower adhesive surface providing the mounting surface per se. In the shown embodiment the housing containing the transcutaneous access device is attached to the base plate as a separate unit, the two elements in combination forming the patch unit. Within the housing a hollow infusion needle 412 is pivotally arranged.

The patch unit comprises first and second openings 415, 416 which may be open or covered by needle penetratable membranes allowing the transcutaneous access device to be provided in a sterile unit inside a sealed patch unit. The transcutaneous access device is in the form of a hollow needle comprising a first needle portion 413 having a first pointed end adapted to penetrate the skin of the subject, the first needle portion extending generally perpendicular to the mounting surface, and a second needle portion 414 in fluid communication with the first needle portion via an intermediate needle portion 415 and having a second pointed end, the second needle portion being arranged substantially in parallel with the mounting surface. The needle is connected to the housing by a mounting means allowing the needle to pivot corresponding to an axis defined by the second needle portion, whereby the needle is moveable between an initial sterile position in which the first needle portion is retracted relative to the mounting surface, and a second position in which the pointed end of the first needle portion projects through the second opening. Alternatively, a soft cannula with an insertion needle may be used in place of the hollow needle, see for example U.S. application 60/635,088 which is hereby incorporated by reference.

The housing further comprises actuation means (not shown) for moving the needle between a retracted and an extended state, and retraction means (not shown) for moving the needle between the extended and a retracted position. The actuation and retraction means are actuated by gripable first and second strip members 421, 422 connected to the respective means through slot-formed openings in the housing, of which the slot 423 for the first strip can be seen. The second strip is further connected to the patch member 432. Arranged on the housing is user-actuatable male coupling means 440 in the form of a pair of resiliently arranged hook members adapted to cooperate with corresponding female coupling means 455 on the pump unit. The housing further comprises an actuator 425 for establishing fluid communication between the pump assembly and the reservoir (see below), and mechanical communication means 426 for activating and de-activating the expelling means.

The pump unit 450 comprises a housing 451 in which a reservoir and expelling means are arranged, the expelling means comprising a pump and actuator assembly 470 of the type described with reference to FIGS. 1-4. The reservoir 460 is in the form of prefilled, flexible and collapsible pouch comprising a needle-penetratable septum 461 adapted to be arranged in fluid communication with the pump assembly via pump inlet 472 when the pump unit is connected to a patch unit for the first time. The housing comprises a window 452 allowing the user to inspect the content of the reservoir.

The control and pump/actuation means, which may be arranged on a PCB or flex-print, comprises in addition to the pump and actuator assembly 470, a microprocessor 483 for controlling, among other, the pump actuation, a contact switch 484 cooperating with the communication means 426 on the patch unit, signal generating means 485 for generating an audible and/or tactile signal, and an energy source 486.

Figure 11:
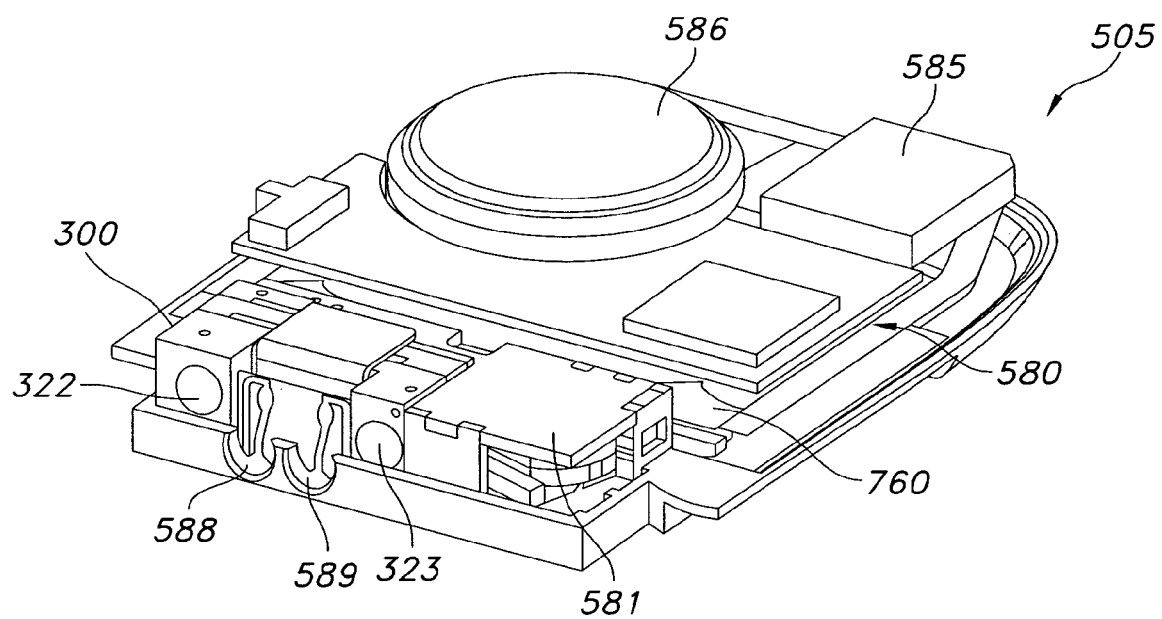
FIG. 11 shows a perspective view of the interior of a pump unit.

FIG. 11 shows a further pump unit with an upper portion of the housing removed. The pump unit comprises a reservoir 760 and an expelling assembly comprising a pump assembly 300 as well as controller means 580 and a coil actuator 581 for control and actuation thereof. The pump assembly comprises an outlet 322 for connection to a transcutaneous access device and an opening 323 allowing a fluid connector arranged in the pump assembly to be actuated and thereby connect the pump assembly with the reservoir. The reservoir 560 is in the form of prefilled, flexible and collapsible pouch comprising a needle-penetratable septum adapted to be arranged in fluid communication with the pump assembly, see below. The shown pump assembly is a mechanically actuated membrane pump, however, the reservoir and expelling means may be of any suitable configuration.

The controller comprises a PCB or flex-print to which are connected a microprocessor 583 for controlling, among other, the pump actuation, contacts 588, 589 cooperating with corresponding contact actuators on the patch unit or the remote unit (see below), position detectors in the actuator, signal generating means 585 for generating an audible and/or tactile signal, a display (if provided), a memory, a transmitter and a receiver allowing the pump unit to communicate with an wireless remote control unit. An energy source 586 provides energy. The contacts may be protected by membranes which may be formed by flexible portions of the housing.

With reference to FIGS. 10 and 11 a modular local unit comprising a pump unit and a patch unit has been described, however, the local unit may also be provided as a unitary unit.

Figure 12:
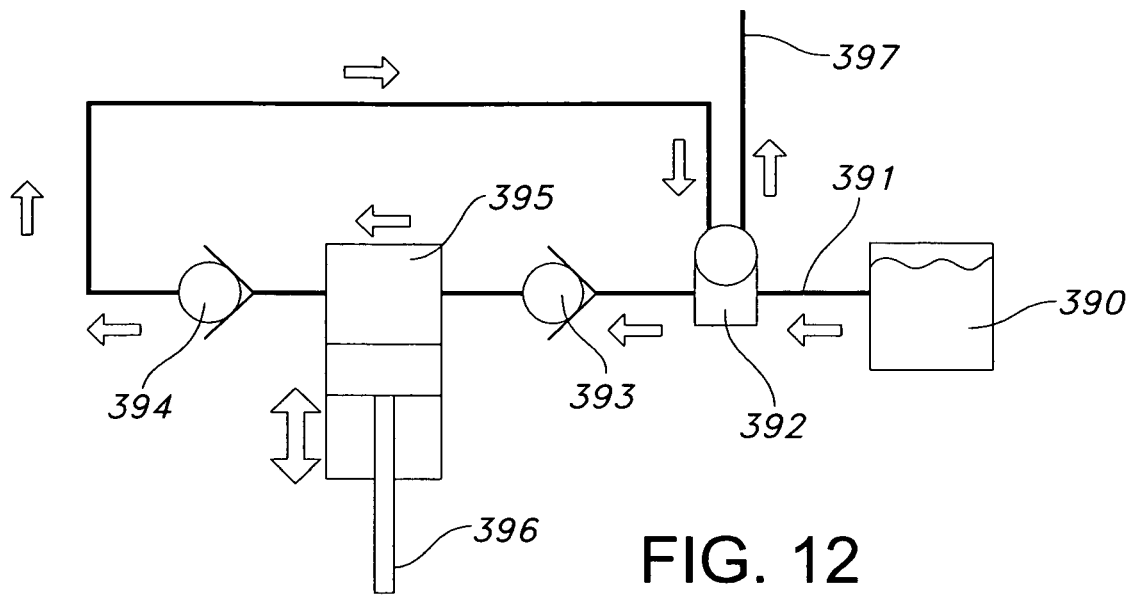
FIG. 12 shows a schematic overview of a pump connected to a reservoir.

With reference to FIG. 12 a schematic overview of a pump assembly connected to a reservoir is shown, the pump assembly comprising the following general features: a fluid inlet 391 in fluid communication with a reservoir 390, a safety valve 392, a suction pump per se having inlet and outlet valves 393, 394 and a pump chamber 395 with an associated piston 396, and an outlet 397. The arrows indicate the flow direction between the individual components. When the piston is moved downwards (in the drawing) a relative negative pressure will build up inside the pump chamber which will cause the inlet valve to open and subsequently fluid will be drawn form the reservoir through the open primary side of the safety valve by suction action. When the piston is moved upwards (in the drawing) a relative overpressure will build up in the pump chamber which will cause the inlet valve to close and the outlet valve and the safety valve to open whereby fluid will flow from the pump chamber through the outlet valve and the secondary side of the safety valve to the outlet. As appears, in normal operation the safety valve allows fluid passage during both intake and expelling of fluid and is thus "passive" during normal operation. However, in case the reservoir is pressurized (as may happen for a flexible reservoir) the elevated pressure in the reservoir will be transmitted to both the primary side of the safety valve and, via the pump chamber, the secondary side of the safety valve in which case the pressure on the primary side of the safety valve will prevent the secondary side to open.

Figure 13:
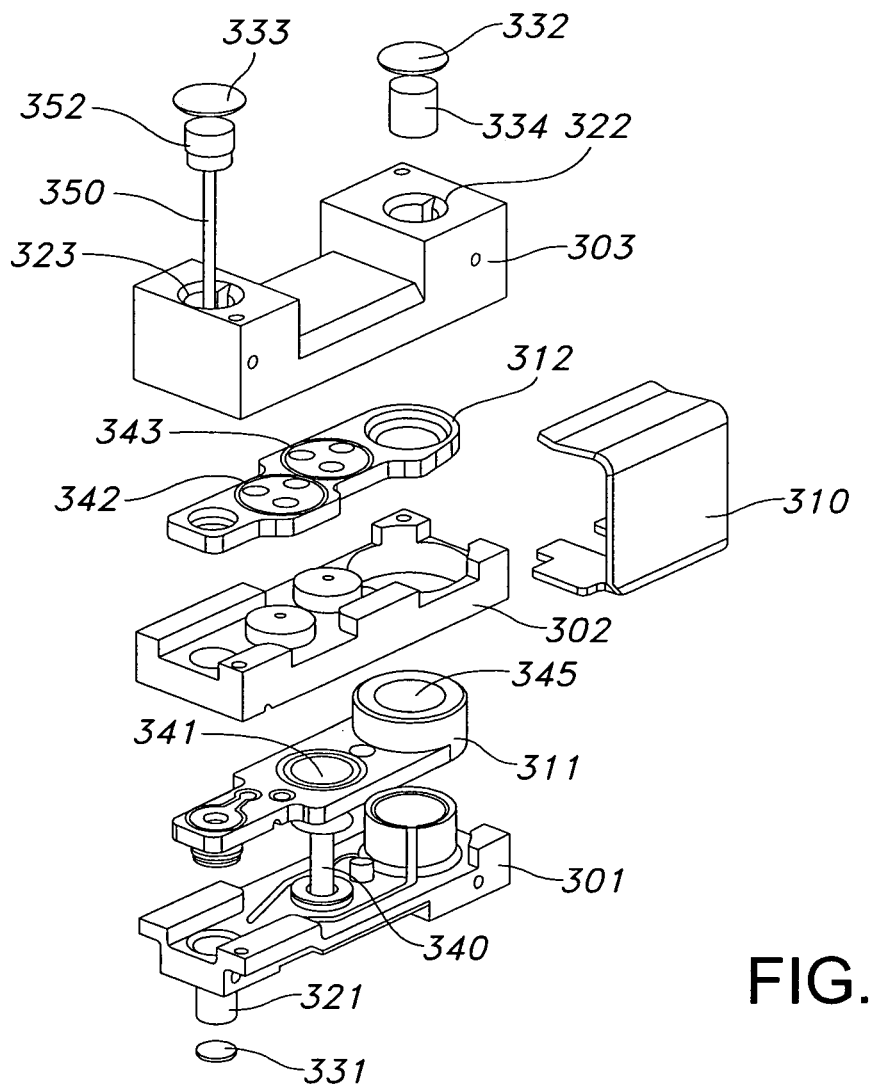
FIG. 13 shows an exploded view of a pump assembly.
Figure 14:
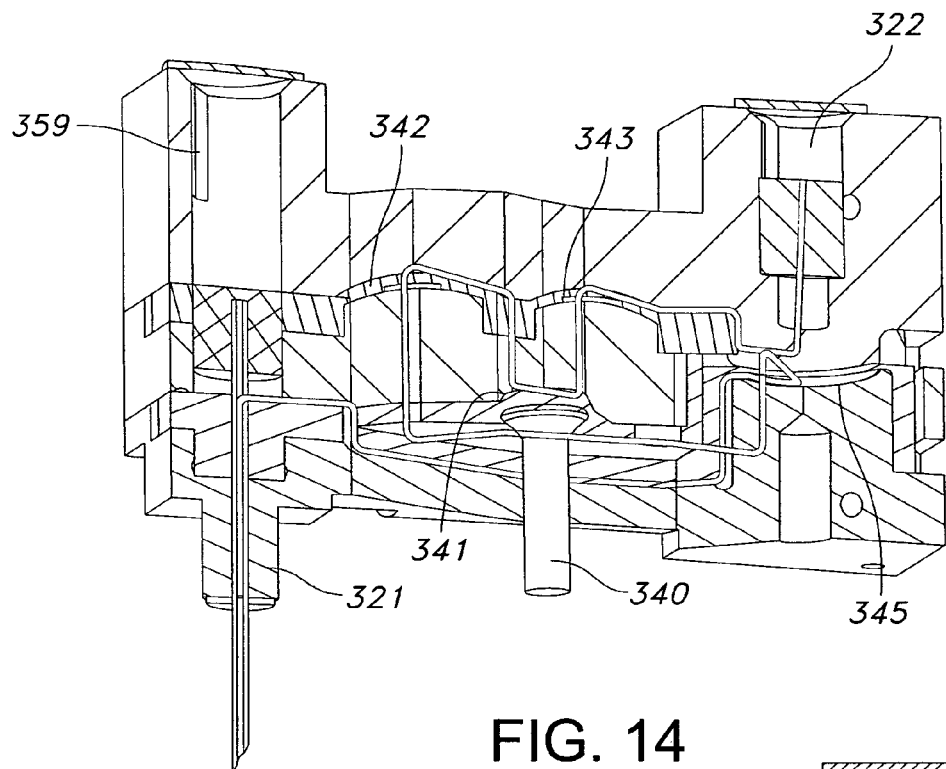
FIG. 14 shows a cross-sectional view of the pump assembly of FIG. 13, FIGS. 15 and 16 show partial cross-sectional views of the pump assembly of FIG. 13.

In FIG. 13 an exploded view of a pump assembly 300 utilizing the pump principle depicted in FIG. 12 is shown, the pump assembly (in the following also referred to as a pump) being suitable for use with the actuators of FIGS. 1-9 and the pump units of FIGS. 10 and 11. The pump is a membrane pump comprising a piston-actuated pump membrane with flow-controlled inlet- and outlet-valves. The pump has a general layered construction comprising first, second and third members 301, 302, 303 between which are interposed first and second membrane layers 311, 312, whereby a pump chamber 341 is formed by the first and second members in combination with the first membrane layer, a safety valve 345 is formed by the first and third members in combination with the first membrane layer, and inlet and outlet valves 342, 343 are formed by the second and third members in combination with the second membrane layer (see FIG. 14). The layers are held in a stacked arrangement by an outer clamp 310. The pump further comprises an inlet 321 and an outlet 322 as well as a connection opening 323 which are all three covered by respective membranes 331, 332, 333 sealing the interior of the pump in an initial sterile state. The membranes are penetratable or breakable (e.g. made from paper) by a needle or other member introduced through a given seal. The outlet further comprises a self-sealing, needle-penetratable septa 334 (e.g. of a rubber-like material) allowing the pump to be connected to an outlet needle. As shown in FIG. 14 a fluid path (indicated by the dark line) is formed between the inlet 321 (see below) and the inlet valve 342 via the primary side of the safety valve 345, between the inlet valve, pump chamber 345 and the outlet valve 343, and between the outlet valve and the outlet 322 via the secondary side of the safety valve, the fluid paths being formed in or between the different layers. The pump also comprises a piston 340 for actuating the pump membrane, the piston being driven by external driving means, e.g. an actuator as shown in FIGS. 1-9.

Figure 15:
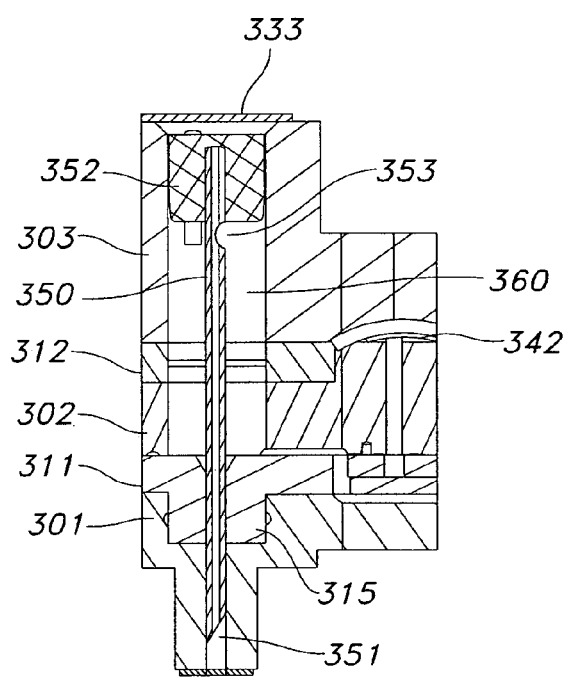

The pump further comprises a fluid connector in the form of hollow connection needle 350 slidably positioned in a needle chamber 360 arranged behind the connection opening, see FIG. 15. The needle chamber is formed through the layers of the pump and comprises an internal sealing septum 315 through which the needle is slidably arranged, the septum being formed by the first membrane layer. The needle comprises a pointed distal end 351, a proximal end on which is arranged a needle piston 352 and a proximal side opening 353 in flow communication with the distal end, the needle and the piston being slidably arranged relative to the internal septum and the chamber. As can be appreciated form FIG. 15 the needle piston in its initial position is bypassed by one or more radially placed keyways 359. These are provided in order to allow steam sterilisation and to vent the air otherwise trapped when the fluid connector is moved forward in the needle chamber.

Figure 16:
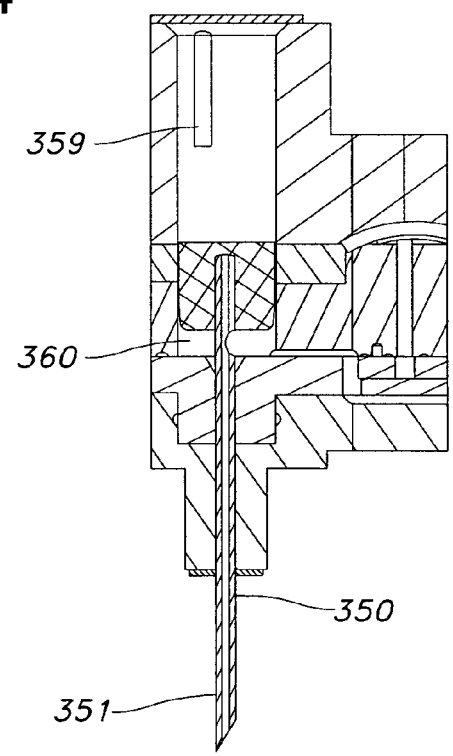

The above-described pump assembly may be provided in a drug delivery device of the types shown in FIGS. 10 and 11. In a situation of use where the pump unit is attached to a patch unit the proximal end 532 of the infusion needle is introduced through the outlet seal and septum 334 of the pump, and the actuator 425 (see FIG. 10) is introduced through the connection membrane 333. By this action the connection needle is pushed from its initial position as shown in FIG. 15 to a actuated position as shown in FIG. 16 in which the distal end is moved through the inlet membrane 331 and further through the needle-penetratable septum of a nearby located reservoir, this establishing a flow path between the reservoir and the inlet valve via the proximal opening 353 in the needle. In this position a seal is formed between the needle piston and the needle chamber.

As appears, when the two units are disconnected, the proximal end 532 of the infusion needle is withdrawn from the pump outlet whereas the connection needle permanently provides fluid communication between the pump and the reservoir.

Figure 17:
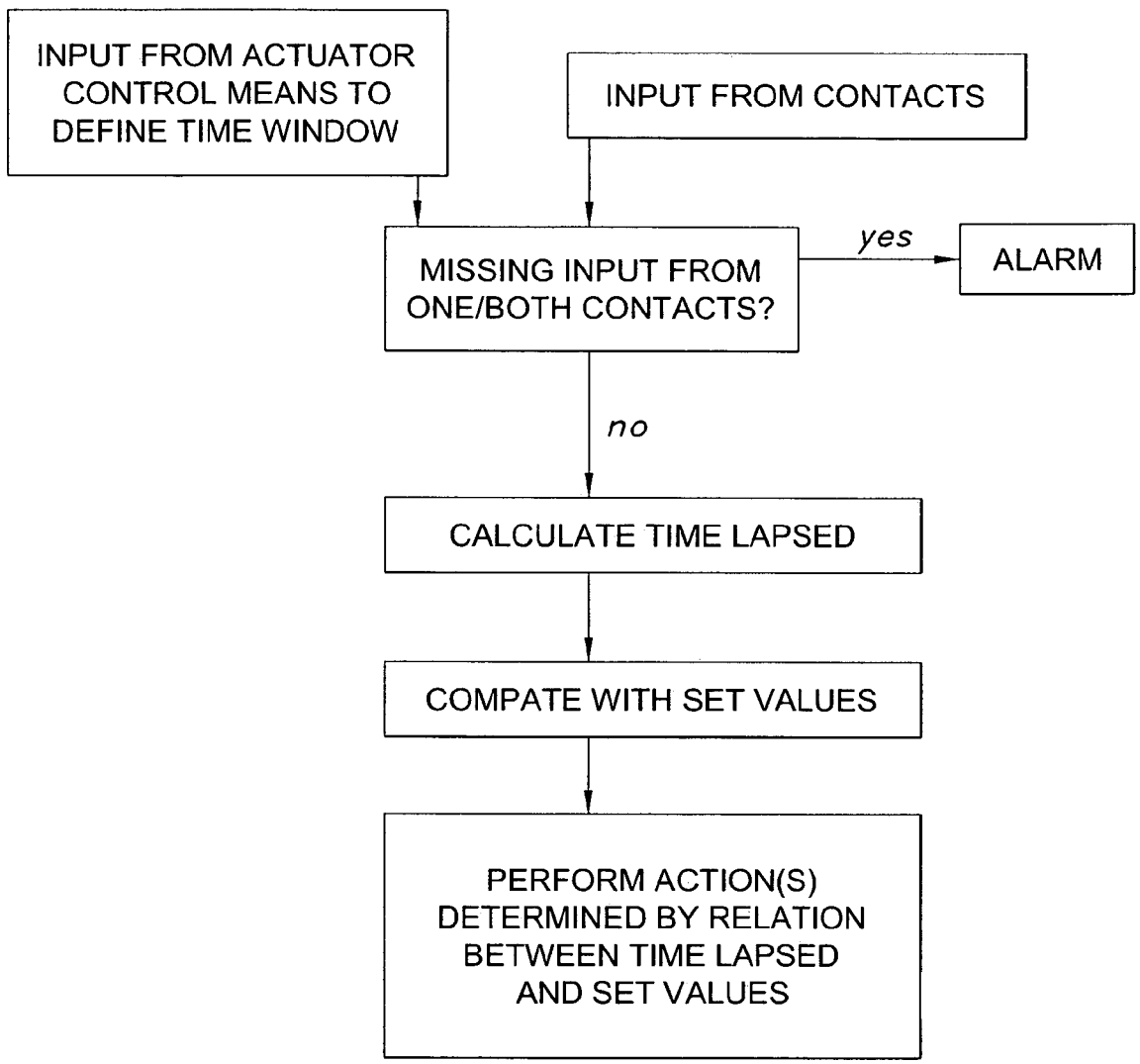
FIG. 17 shows a diagram representing controller evaluation of actuator derived information.

Turning to the above-mentioned operation and performance control by means of elapsed time detection for actuator lever movement between an initial and an actuated position or vice versa, FIG. 17 shows a flow chart illustrating the sequence of operations carried out for an implementation of this principle. More specifically, signals provided from sensors or switches adapted to detect that an actuator member (here: the lever) or a component functionally coupled to the actuator such as the above-described piston which is considered a part of the actuator although it may be integrally formed with the pump) has reached its initial respectively actuated position during an actuation cycle is fed to a processor (e.g. microprocessor). The sensors/switches may be of any suitable type, e.g. electrical, optical or magnetic. If the initial and/or the actuated position cannot be detected, the processor detects an error condition which may be related to the type of non-detection. For example, when the actuator is used for the first time, non-detection of one or both signals may be indicative of an inherent fault in the actuator/pump/device and a corresponding alarm condition may be initiated. In most cases it will be relevant to define a time window within which the two positions have to be detected during an actuation cycle, this in respect of both the actuation movement between the initial and actuated position and the return movement between the actuated and initial position. Correspondingly, if the time lapsed between the detection of an initial-to-actuated or actuated-to-initial movement falls outside the time window an alarm condition indicating a malfunctioning may be initiated as will be described in the following with reference to a number of examples. When calculating the time lapsed this may be based on two "real time" time stamps or a timer may be used when movement between the two positions is initiated.

Turning to "normal" operation conditions, the lapsed time for movement between the initial and the actuated position (or between the actuated and the initial position) is calculated and compared with set time value ranges (e.g. pre-set or calculated ranges). Depending on the relation between the time lapsed and the set time value ranges a given pre-defined signal (or non-signal) is output from the processor which may then be utilized to perform a given action relevant for the device or system in which the actuator and control system is implemented.

Whereas a general example of an actuator operation and performance control principle has been described above, a more specific implementation of the principle will be described with reference to a drug delivery device of the type described above.

During operation of the pump after priming of an initially empty pump, liquid drug is sucked from the flexible reservoir into the pump chamber as the piston/actuator returns from an actuated to an initial position, whereas liquid drug is pumped from the pump chamber out through the transcutaneous access device as the piston/actuator is moved from the initial to the actuated position. During normal operation of the pump the time used for both of these pump strokes can be assumed to be near-constant as the conditions remain substantially unchanged. However, during operation of the pump certain conditions may arise which will influence operation of the pump and thereby potentially also of the amount of drug delivered. A major concern associated with infusion of drugs is occlusion of the access device.

A problem with existing drug delivery pumps is their ability to detect occlusions, especially when the pump is used for low flow applications. The problem is caused by the combination of low flow and compliance of the pump as it can take several hours for a blocked pump to build up enough pressure before the occlusion detector gives an alarm. Many traditional delivery pumps are compliant because the reservoir is part of the pump mechanism and/or because the fluid passage from the pump to the point of delivery (e.g. the distal end of an infusion needle) is compliant.

Using a membrane pump as a suction pump in a drug delivery device, a hydraulically much stiffer system can be achieved as the reservoir is "behind" the pump. Correspondingly, by also paying attention to the compliance of the outlet portion of the system a very stiff system may be provided such that an eventual occlusion will give an instant pressure increase, making it possible to alarm the user of an occlusion significantly faster than with traditional pumps. However, instead of providing an additional pressure sensor, the present invention can utilize that occlusion downstream of the pump will result in longer pump cycles for the outlet stroke given the same force is applied from the pump membrane actuator.

A further condition that would be desirable to detect would be under-dosing due to backflow of drug to the reservoir during the expelling stroke in case of malfunctioning of the inlet valve, e.g. when drug particles are captured in the valve. For such a condition it can be expected that the outlet stroke cycle will be shorter as a portion of the drug in the pump chamber is pumped backwards through the open inlet valve. In addition, this situation may also result in a shortened suction stroke as flow resistance through the open inlet valve may be reduced. On the other hand, in case of (partial) inlet valve occlusion, the suction stroke will result in longer cycle times. A longer suction stroke time may also be indicative of the reservoir being (close to) empty.

As the pump unit of FIGS. 10-16 is supplied with both a sealed reservoir and a sealed pump, it is necessary to prime the pump with liquid drug when a new pump unit is connected to a patch unit for the first time. Correspondingly, when the pump controller detects this condition, a priming cycle is initiated. For example, the pump may be operated for a given number of cycles corresponding to the volume of the pump where after it is assumed that no gas remains in the pump. As gas has a much lower viscosity than a liquid drug, it can be assumed that a pump partially filled with air will have shortened cycle times for inlet and/or the outlet strokes. Correspondingly, by monitoring the cycle times during priming it can be controlled that the pump has been properly primed. For example, a priming cycle is started whereby the pump is actuated in accordance with a predetermined priming cycle frequency, and a first series of time lapsed values (in the following also time value or T) for movement of the pump membrane actuator associated with the pumping of a gas or a mixture of gas and liquid is detected. The detected time values are compared with a value associated with the pumping of a liquid. The latter may either be pre-defined or be calculated dynamically on the basis of the values detected by a series of pump strokes known to represent the pumping of air. In case the time values for a dry and a wet pump are similar, the controller may use another condition to determine that the pump has been properly primed, e.g. a rise in time values due to pumping of liquid though a restriction in the flow conduit downstream of the pump, or due to the liquid entering the subcutaneous tissue of the user. In case the detected values (i.e. one or more) are within the pre-specified or calculated range, the priming cycle is ended. In case the detected values are not within the range, the priming cycle continues. In case the primed condition is not identified within a given pre-defined period, a malfunction condition can be identified. For the time values the suction stroke, the expelling stroke or both may be used as a basis for determining whether priming has taken place successfully. Alternatively, instead of comparing the detected time values with a preset or calculated specific value, it would also be possible to operate the pump until a steady state was achieved, i.e. the time pattern for a pre-defined number of operations vary within only a pre-defined range.

The processor should be adapted for compensating for "normal" bounce of the sensors/switches, however, excessive bouncing may be registered as a malfunctioning condition. Further, registering passive movement of the actuator during non-actuated periods may also be utilized to register a malfunctioning condition.

With reference to FIGS. 18-22 a number of examples based on experiments conducted with a prototype version of the pump assembly shown in FIGS. 13-16 will be described. Each data pump represents an actuation of the coil actuator.

EXAMPLE 1

Sticking Valves

Figure 18:
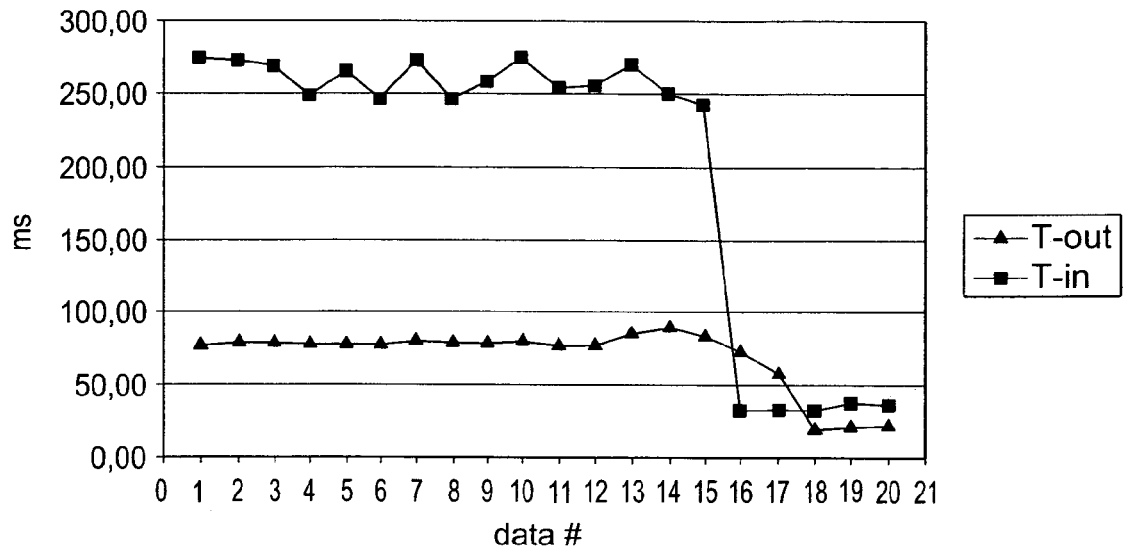
FIGS. 18-22 show T-in and T-out values in milliseconds (ms) for different pump conditions during actuation of a pump.

In order to get very tight valves the surfaces of the valve seats as well as the rubber membranes are polished. This leads to sticking between the valve seat and the membrane. This phenomenon was reflected on the pump stroke duration measurements as shown in FIG. 18. At data points #1-15 a freshly assembled, dry pump is pumping air. The valves are sticking which is why the stroke durations are relatively high. At data point #16 the inlet valve gets wet which eliminates the sticking and a fall in inlet stroke duration is seen. A few strokes later the liquid reaches the outlet valve with a similar effect on outlet stroke duration.

EXAMPLE 2

Priming Detection

Figure 19:
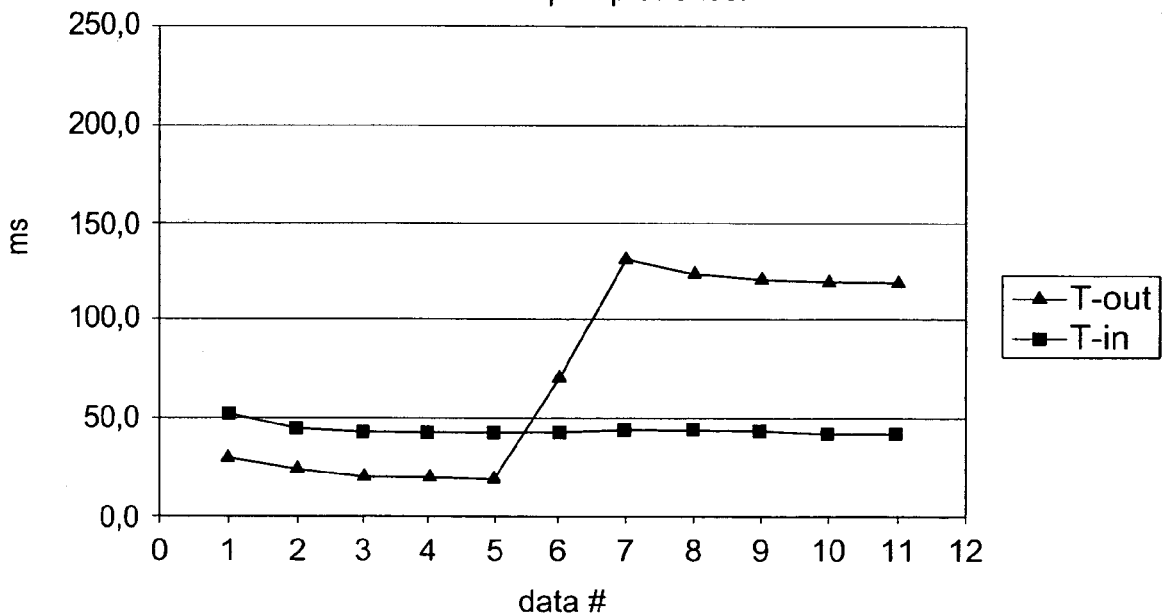

FIG. 19 shows the duration of a series of output strokes and a series of input strokes. Data #1-5 shows filling of the conduit connecting the pump to a transcutaneous access device in the form of a hollow hypodermic needle. Output strokes are faster than input strokes because the output stroke is driven by an actuator delivering a high force compared to the input stroke which is driven by the elastic force of the pump membrane itself. At data point #5, the liquid reaches the needle (ID 0.15 mm, 40 mm long) which represents a significantly higher fluid resistance than the connecting channel (ID 0.50 mm) between the pump and the needle. At this point a significant rise in output stroke duration (T-out) is observed. No change is observed at the input stroke duration (T-in). At data point #7 the needle is completely filled, which is why the output stroke duration stabilizes at a new level. This shift in output stroke duration can be used to determine when the pump is primed. In case a larger-bore cannula is used as an alternative to a hypodermic needle, a hollow needle may still be used, e.g. to connect a pump unit with a patch unit.

EXAMPLE 3

Occlusion Detection

Figure 20:
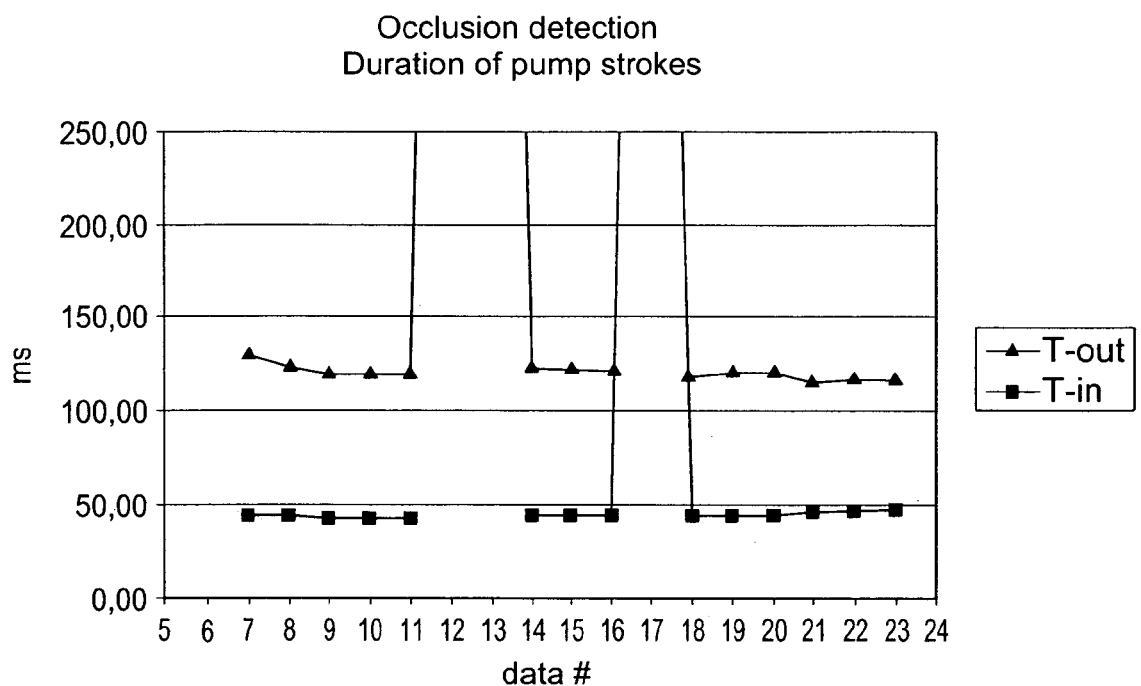

FIG. 20 shows what happens if the inlet or the outlet from the pump is occluded. Data points #7-11 show the duration of outlet stroke and inlet stroke when the needle of example 2 is filled with liquid and neither inlet nor outlet is blocked. At data point #11 the outlet is blocked. At the following pump stroke the actuator does not reach its bottom stop position, or does it with a considerable delay. This signal can be used for a very fast and early detection of outlet occlusion. At data point #14 the blocking of the outlet is removed. At data point #16 the inlet is blocked. At the following pump stroke the actuator does not reach its top stop position. This signal can be used for detection of occlusions on the pump inlet. The latter can also be used to detect that a flexible reservoir is close to empty, however, in such a case the rise in T-in will be less dramatic with only a slow rise, but may still be sufficient to detect a close-to-empty reservoir condition.

EXAMPLE 4

Bubble Detection

Figure 21:
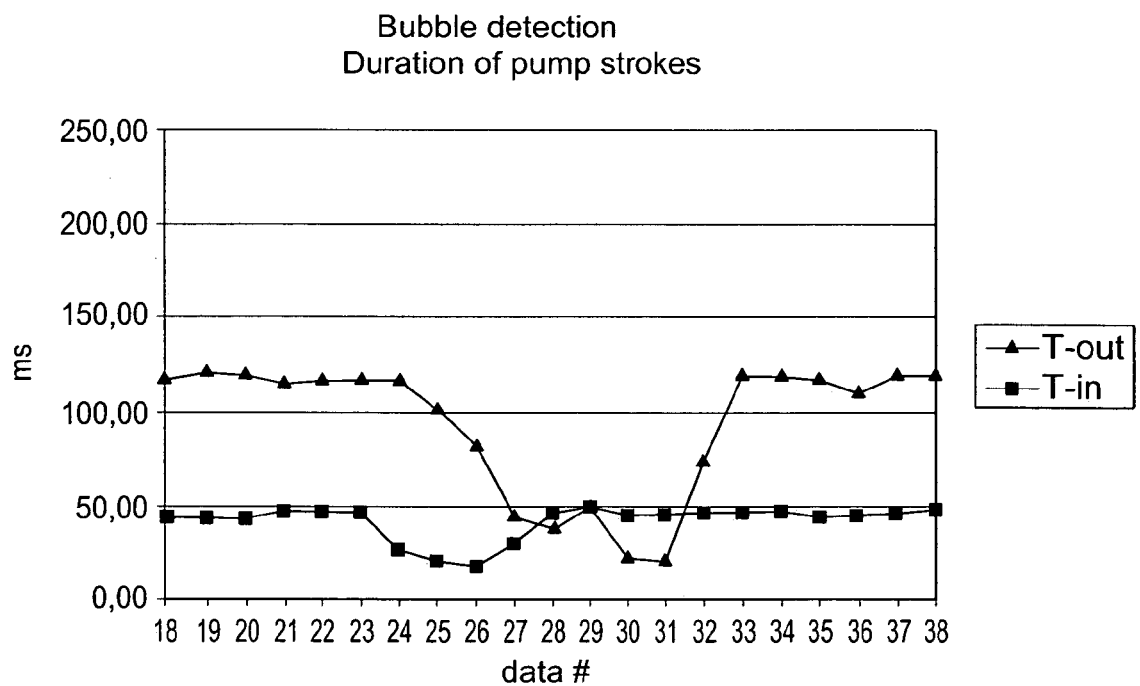

FIG. 21 shows what happens if a bubble is passing through the pump. Data points #18-23 show the normal situation where the patient needle is filled with liquid and no bubbles are present in the pump. At data point #23 an air bubble enters the pump inlet. At this point the inlet stroke duration lowers significantly due to the lower viscosity of air compared to liquid, e.g. insulin. At data point #24 the same effect is seen at the outlet stroke duration. At data point #28 all rests of the bubble is cleared from the inlet channel and at data point #33 all bubble rests are cleared from the outlet channel. In both cases the shift from partly air (bubble) to no air gives leads to a significant rise in stroke duration because of the different viscosity. One of these signals or a combination of them can be used for detecting if a bubble is entering or passing through the pump. Although a single bubble may not represent a malfunctioning of the pump or the pump-reservoir system, the above example shows that the principles of the present invention can be used to detect even very minor events.

EXAMPLE 5

Air Detection

Figure 22:
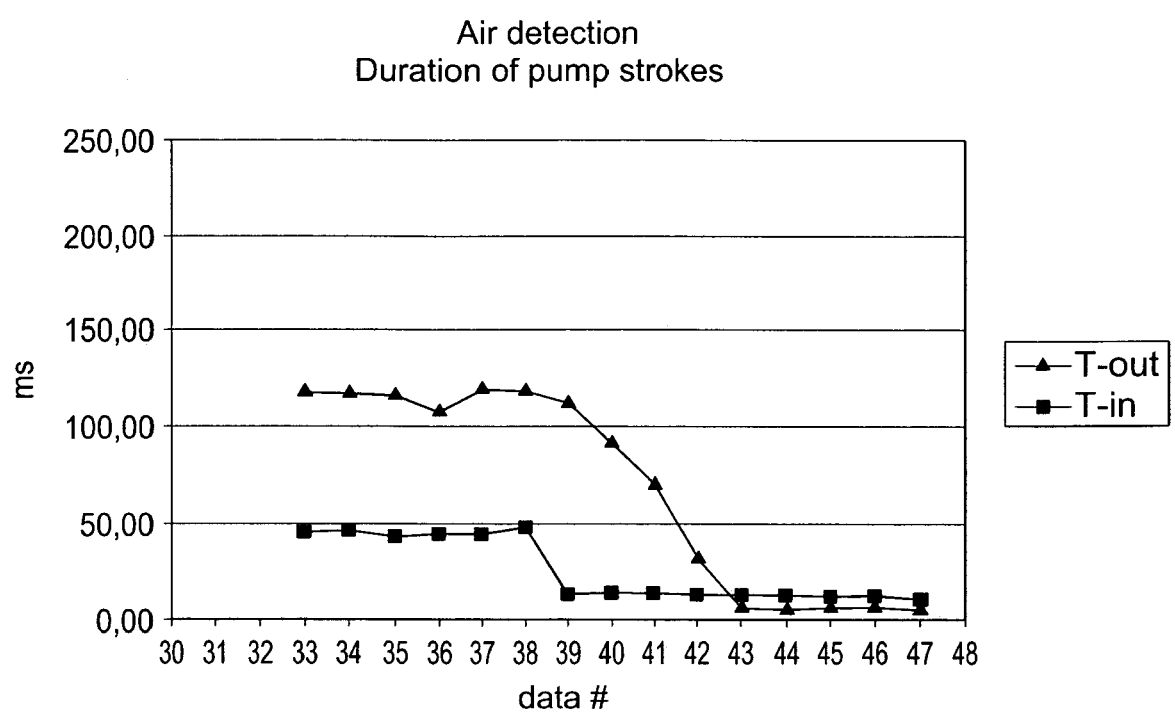

FIG. 22 shows what happens when the pump starts to pump air instead of liquid, e.g. insulin, which may happen when the flexible reservoir disengages from the pump inlet or when a major air leak develops between the pump and the reservoir. Data points #33-38 show normal pumping with a pump and needle filled with liquid. At data point #38 air enter the inlet and one or two pump strokes later it reaches the outlet channel. This is in both cases seen as a significant fall in pump stroke duration due to the significant difference in viscosity between liquid and air.

EXAMPLE 6

Dynamic Range Calculation

Dependent upon the actual design of a given pump, it may be found that there is only minimal variation between the pumps and that substantially the same time values are detected when pumping e.g. dry or wet. For such a pump design it may be desirable to use pre-set time ranges. However, for a different pump design there may be some variation between the individual pumps for which reason it may be desirable to calculate a set of time ranges for the individual pump based on well-defined pump conditions. For example, if the pump characteristics are different for a dry and a wet pump as shown in FIG. 18, the first e.g. 10 strokes may be used to calculate an average "dry" value which then forms an open range for defining when the pump has been filled and reached its "wet" stage. The wet range may be defined by a factor, e.g. a T-in drop of 50% or more, or a numeric value, e.g. a T-in drop of 100 milliseconds (ms) or more. The wet value used for comparison may be calculated as an average of a number of individual values. In case a pump or a pump-patch combination comprises a downstream constriction in the flow path, e.g. a narrow hollow needle, an average value (defining an open-ended range) based on wet values before the liquid reaches the flow constriction may be used to determine when the liquid has filled the constriction, see FIG. 19. Correspondingly, such a value may also be used to determine when the fluid enters the subcutaneous tissue of a patient as this may again change the detected values.

In the above embodiments the time lapsed between two end positions is measured, however, one or more additional contacts may be provided to provide further information in respect of actuator movement during an actuator stroke and thereby allowing the system to detect a further number of conditions. The additional contacts may be without mechanical contact (e.g. optical or magnetic) in order not to impair free movement of the actuator. Thus, for any additional contact one or more additional sets of defined time ranges may be defined, each time range being associated with movement of the actuator member in a given direction between two given positions and a given actuation force. For example, a near-initial switch could be used to continuously estimate characteristics which are more related to pump/membrane properties than pump resistance, e.g. altering of the pump membrane properties due to prolonged contact with a given drug. In this it will be possible to adapt the pump actuation to the new pump properties.

In the above examples the relation between pump actuation and pump member movement has been discussed, however, during normal operation of an infusion pump the user will normally not relate to the actual pump stroke pattern as dispensing of drug may be based on volume, e.g. an amount measured in ml or a rate measured in ml per hour, or it may be based on units of active drug in a given formulation, e.g. a bolus of insulin measured in units, or an infusion rate of insulin measured in units per hour, which is then used to calculate the corresponding number and the pattern for actuation of the coil.

In addition to the above principles for detection of pump/actuator conditions, by measuring the delivered energy to empty the pump chamber it is possible to calculate the relative counter pressure in the pump. This energy can be measured by obtaining the integral of current*voltage by time for the movement or it can be calculated by counting the number of necessary current pulses or the number of timeslots necessary to move the piston from top to bottom or simply as the time duration if DC current and DC voltage are applied. Indeed, in order to determine pressure based on e.g. P*V the energy consumed by e.g. friction and initial pump stretching should be deducted. The calculated counter pressure or a specific limit for delivered energy to empty the pump chamber can be used as an indication of occlusion and used as a trigger for an occlusion alarm signal. The calculated counter pressure can also be used to compensate for mechanical counter pressure sensitivity in the volumetric accuracy of the pump system by changing the pump frequency depending on the counter pressure or the time duration to the next pump stroke. As for the expelling-stroke energy also the energy for the suction-stroke can be measured in case the pump is actuated correspondingly. This can also be used to indicate abnormal behaviour in the pump system including the valves. The calculated counter pressure can be used to decide and optimise the control of the next piston movement during the stroke assuming a slow counter pressure variation by time, e.g. size of current or slope in current ramp or duty cycle in pulse width modulation of current.

Instead of extra contacts/switches for initial, actuated and in-between positions, the system can be designed to monitor the driving power of the piston excitation system during the movement of the piston, e.g. timely monitoring of the current and/or the voltage or a special electrical measuring signal (e.g. AC signal) can be superposed on the driving signal and the corresponding signals generated can be picked up by an additional coil.

When the pump described with reference to FIGS. 10-16 is used for the first time, the pump is initially empty and air is pumped. As air has a very low viscosity, pumping of air can be used to detect properties of the pump system. For example, when the pump is primed the energy necessary for driving the pump membrane between its initial and actuated positions can be determined. When the energy necessary for driving the pump membrane between its initial and actuated positions when liquid is pumped subsequently is determined, the difference between the energies can be used to calculate the energy used for the pump work and thus the pressure in the pump system.

Figure 23:
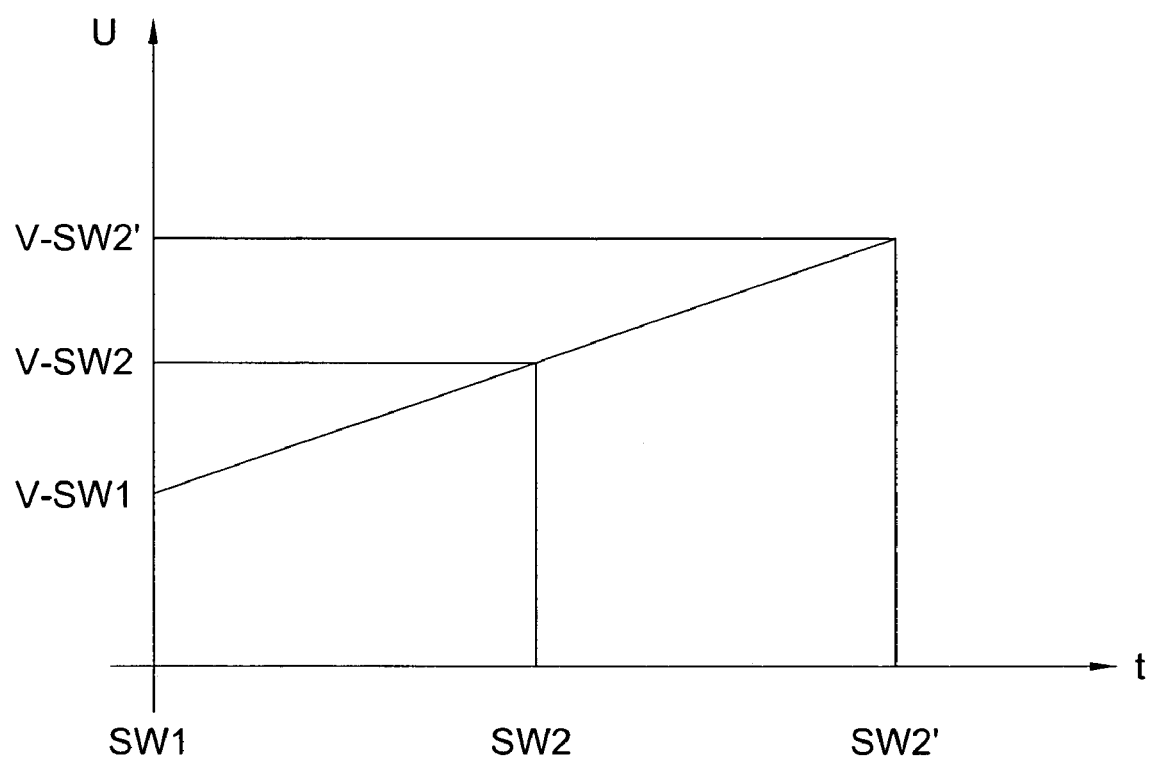
FIG. 23 shows in principle a voltage/time relationship during pump actuation.

Referring to FIG. 23 a principle example of pump actuation during priming and subsequent normal operation is shown. When the pump is first actuated, the voltage is slowly ramped up until the actuator starts moving and the first switch is thereby actuated at SW1, this indicating that static friction in the pump/actuator system as well as eventual pre-tension in the pump membrane has just been overcome at V-SW1. When the voltage is further ramped up, the elastic pump membrane is stretched until it reaches its end position corresponding to the actuator end position whereby the second switch is actuated at SW2. The voltage V-SW2 necessary for this movement is thus indicative of pump losses during pumping essentially without load. As liquid is subsequently entering the pump, the voltage is further ramped up during each pump stroke until a primed state is reached for which a voltage V-SW2' is used to fully activate the pump. Based on the difference between V-SW2 and V-SW2' the energy necessary for the actual pump work and thus the pump pressure may be determined.

Although a linear voltage-time relationship is shown in FIG. 23, a non-linear relationship may prevail under actual pump conditions. Further, when the pump is actuated under normal operation conditions a ramp with a different profile may be used, e.g. the ramp may be adjusted to achieve a given pump cycle timing under which the pump operates most efficiently, e.g. to ensure that the valves operate efficiently with minimum back-flow. Indeed, instead of ramping the voltage also the current may be ramped.

In the above description of the exemplary embodiments, the different structures providing the described functionality for the different components have been described to a degree to which the concepts of the present invention will be apparent to the skilled reader. The detailed construction and specification for the different structures are considered the object of a normal design procedure performed by the skilled person along the lines set out in the present specification. For example, the individual components for the disclosed embodiments may be manufactured using materials suitable for medical use and mass production, e.g. suitable polymeric materials, and assembled using cost-effective techniques such as bonding, welding, adhesives and mechanical interconnections.

The invention claimed is:

1. A pump assembly comprising:
an actuator lever comprising a support portion and an arm portion having a longitudinal extent,
an actuator for moving the actuator lever, at least a part of the actuator being attached to the support portion of the actuator lever,
a supporting structure,
a pump comprising a pump member moveable by actuation of the actuator lever, wherein the pump is adapted to pump a liquid between an inlet and an outlet thereof,
the pump inlet is adapted to be arranged in fluid communication with an outlet of a reservoir adapted to contain a fluid drug,
the pump outlet is adapted to be arranged in fluid communication with a transcutaneous access device,
the pump member performing a pump stroke when actuated by the actuator lever, and wherein the pump further comprises inlet and outlet valves associated with the pump inlet and the pump outlet respectively, and a pump chamber abutting the pump member, the pump member is adapted to perform a pump stroke and a suction stroke when moved between a first and a second position respectively, wherein the pump chamber is caused to contract and expand due to the movement of the pump member,
a first stationary pivoting joint formed between the actuator lever and the supporting structure and located at a proximal end of the arm portion of the actuator lever,
a second floating pivoting joint formed between the actuator lever and the pump member and located between the first stationary pivoting joint and the support portion of the actuator lever, the second floating pivoting joint allowing the pump member to float relative to the actuator lever, a constant-length actuator arm being defined by a portion of the arm portion of the actuator lever formed between the first stationary pivoting joint and the second floating pivoting joint,
wherein the second floating pivoting joint is comprised of a lever joint structure on the arm portion of the actuator lever that cooperates with a substantially planar surface of the pump member, the second floating pivoting joint allowing the actuator lever and the lever joint structure to float relative to the planar surface.

2. A pump assembly as in claim 1 wherein a biasing member is provided and adapted to hold the actuator lever and the supporting structure at the first pivoting joint, and the actuator lever and the pump member at the second floating pivoting joint in contact, respectively, with each other.

3. A pump assembly as in claim 1, wherein the actuator is a coil-magnet actuator, the coil and magnet(s) being arranged on the actuator lever and the supporting structure respectively.

4. A pump assembly as in claim 1, wherein the actuator lever is moved between a first position and a second position, the pump assembly further comprising first and second stop means adapted to engage the actuator lever in the first and the second position respectively.

5. A pump assembly as in claim 4, further comprising:
   detection means for detecting when the actuator lever has moved to the first and second positions respectively and supplying time signals indicative thereof, and
   a controller for determining on the basis of supplied time signals the time lapsed when the actuator lever is moved between the first and second positions in a given direction, the controller comprising information representing at least one defined time range, each time range being associated with movement of the actuator lever in a given direction between the first and second positions and a given actuation force, the controller being adapted to compare the determined time lapsed with the defined time range(s) and perform an action corresponding to the time range associated with the determined time lapsed.

6. A pump assembly as in claim 1, wherein the transcutaneous access device comprises a distal end adapted to be inserted through the skin of a subject, the transcutaneous access device comprising an inlet in fluid communication with or being adapted to be arranged in fluid communication with the pump outlet.

7. A pump assembly comprising:
   an actuator lever comprising a support portion and an arm portion having a longitudinal extent,
   an actuator for moving the actuator lever, at least a part of the actuator being attached to the support portion of the actuator lever,
   a supporting structure,
   a pump comprising a pump member moveable by actuation of the actuator lever, wherein the pump is adapted to pump a liquid between an inlet and an outlet thereof,
   the pump inlet is adapted to be arranged in fluid communication with a transcutaneous access device,
   the pump member performing a pump stroke when actuated by the actuator lever, and wherein the pump further comprises inlet and outlet valves associated with the pump inlet and the pump outlet respectively, and a pump chamber abutting the pump member, the pump member is adapted to perform a pump stroke and a suction stroke when moved between a first and a second position respectively, wherein the pump chamber is caused to contract and expand due to the movement of the pump member,
   a first floating pivoting joint formed between the actuator lever and the supporting structure allowing the actuator lever to float relative to the supporting structure and located at a proximal end of the arm portion of the actuator lever,
   a second floating pivoting joint formed between the actuator lever and the pump member and located between the first floating pivoting joint and the support portion of the actuator lever, the second floating pivoting joint allowing the actuator level to float relative to the pump member, a constant-length actuator arm being defined by a portion of the arm portion of the actuator lever formed between the first floating pivoting joint and the second floating pivoting joint,
   wherein at least one of the first and the second floating pivoting joints is comprised of a lever joint structure on the arm portion of the actuator lever that defines one of a line or a point of contact that cooperates with a substantially planar surface on at least one of the pump member and the supporting structure respectively,
   wherein at least one of the first and the second floating pivoting joints allows the actuator lever and the lever joint structure to float relative to the planar surface of at least one of the pump member and the supporting structure respectively.

8. A pump assembly comprising:
   an actuator lever comprising a support portion and an arm portion having a longitudinal extent,
   a supporting structure,
   a pump comprising a pump member moveable by actuation of the actuator lever,
   an actuator for moving the actuator lever wherein the actuator is a coil-magnet actuator, at least a part of the actuator being attached to the support portion of the actuator lever,
   a first stationary pivoting joint formed between the actuator lever and the supporting structure and located at a proximal end of the arm portion of the actuator lever,
   a second floating pivoting joint formed between the actuator lever and the pump member and located between the first stationary pivoting joint and the support portion of the actuator lever, the second floating pivoting joint allowing the pump member to float relative to the actuator lever, a constant-length actuator arm being defined by a portion of the arm portion of the actuator lever formed between the first stationary pivoting joint and the second floating pivoting joint,
   wherein the second floating pivoting joint is comprised of a lever joint structure on the arm portion of the actuator lever that cooperates with a substantially planar surface of the pump member, the second floating pivoting joint allowing the actuator lever and the lever joint structure to float relative to the planar surface of the pump member.

9. A pump assembly as in claim 8, wherein the coil and the magnet(s) are arranged on the actuator lever and the supporting structure respectively.

10. A pump assembly comprising:
   an actuator lever comprising a support portion and an arm portion having a longitudinal extent,
   a supporting structure,
   a pump comprising a pump member moveable by actuation of the actuator lever,
   an actuator for moving the actuator lever wherein the actuator is a coil-magnet actuator, at least a part of the actuator being attached to the support portion of the actuator lever,
   a first floating pivoting joint formed between the actuator lever and the supporting structure and located at a proximal end of the arm portion of the actuator lever, the first floating pivoting joint allowing the actuator lever to float relative to the supporting structure,
   a second floating pivoting joint formed between the actuator lever and the pump member and located between the first floating pivoting joint and the support portion of the actuator lever, the second floating pivoting joint allowing the actuator lever to float relative to the pump member, a constant-length actuator arm being defined by a portion of the arm portion of the actuator lever formed between the first floating pivoting joint and the second floating pivoting joint, wherein at least one of the first and second floating pivoting joints is comprised of a lever joint structure on the arm portion of the actuator lever that defines one of a line or a point of contact that cooperates with a substantially planar surface on at least one of the pump member and the supporting structure respectively, wherein at least one of the first and the second floating pivoting joints allows the actuator lever and the lever joint structure to float relative to the planar surface of at least one of the pump member and the supporting structure respectively.

11. A pump assembly as in claim 10, wherein the coil and magnet(s) are arranged on the actuator lever and the supporting structure respectively.

* * * * *